United States Patent
Chang et al.

(10) Patent No.: US 9,951,072 B2
(45) Date of Patent: Apr. 24, 2018

(54) COMPOSITIONS AND METHODS FOR INHIBITING BETA-LACTAMASE

(71) Applicant: LegoChem Biosciences, Inc., Daejeon (KR)

(72) Inventors: Hye Kyung Chang, Daejeon (KR); Sung Yoon Baek, Daejeon (KR); Min Jung Kim, Daejeon (KR); Kyu Man Oh, Daejeon (KR); Jeung Soon Choi, Daejeon (KR); Soo Bong Ha, Daejeon (KR); Sung Min Kim, Daejeon (KR); Chul-woong Chung, Daejeon (KR); Dae Hyuck Kang, Daejeon (KR); Hyun Jin Kwon, Daejeon (KR); Young Lag Cho, Daejeon (KR); Yong Zu Kim, Daejeon (KR)

(73) Assignee: LegoChem Biosciences, Inc., Daejeon (KR)

( * ) Notice: Subject to any disclaimer, the term of this patent is extended or adjusted under 35 U.S.C. 154(b) by 0 days.

(21) Appl. No.: 15/281,355

(22) Filed: Sep. 30, 2016

(65) Prior Publication Data

US 2017/0096430 A1  Apr. 6, 2017

Related U.S. Application Data

(60) Provisional application No. 62/236,228, filed on Oct. 2, 2015.

(51) Int. Cl.
*C07D 471/08* (2006.01)
*A61K 31/46* (2006.01)
*C07D 519/00* (2006.01)

(52) U.S. Cl.
CPC ............ *C07D 471/08* (2013.01); *A61K 31/46* (2013.01); *C07D 519/00* (2013.01)

(58) Field of Classification Search
CPC ..... C07D 471/08; C07D 519/00; A61K 31/46
See application file for complete search history.

(56) References Cited

U.S. PATENT DOCUMENTS

| | | |
|---|---|---|
| 2003/0199541 A1 | 10/2003 | Lampilas et al. |
| 2005/0020572 A1 | 1/2005 | Aszodi et al. |
| 2010/0087648 A1 | 4/2010 | Lampilas et al. |
| 2013/0274475 A1 | 10/2013 | Mangion et al. |
| 2013/0281359 A1 | 10/2013 | Maiti et al. |
| 2013/0289012 A1 | 10/2013 | Gu et al. |
| 2013/0296555 A1 | 11/2013 | Gu et al. |
| 2013/0345190 A1 | 12/2013 | Gu et al. |
| 2014/0275001 A1 | 9/2014 | Hwang et al. |
| 2014/0288064 A1* | 9/2014 | Bhagwat ............... A61K 31/46 514/230.5 |
| 2015/0038478 A1 | 2/2015 | Gu et al. |
| 2015/0038479 A1 | 2/2015 | Gu et al. |
| 2015/0038482 A1 | 2/2015 | Gu et al. |
| 2015/0111864 A1 | 4/2015 | Garad et al. |
| 2015/0141401 A1 | 5/2015 | Abe et al. |

FOREIGN PATENT DOCUMENTS

| | | |
|---|---|---|
| WO | WO-2009091856 A2 | 7/2009 |
| WO | WO-2013/038330 A1 | 3/2013 |
| WO | WO-2013030733 A1 | 3/2013 |
| WO | WO-2013030735 A1 | 3/2013 |
| WO | WO-2013149121 A1 | 10/2013 |
| WO | WO-2013149136 A1 | 10/2013 |
| WO | WO-2013150296 A1 | 10/2013 |
| WO | WO-2013180197 A1 | 12/2013 |
| WO | WO-2014091268 A1 | 6/2014 |
| WO | WO-2014141132 A1 | 9/2014 |
| WO | WO-2015/110963 A1 | 7/2015 |

OTHER PUBLICATIONS

International Search Report dated Feb. 13, 2017 in International Application No. PCT/IB2016/001508.

* cited by examiner

*Primary Examiner* — Pancham Bakshi
(74) *Attorney, Agent, or Firm* — Foley Hoag LLP; David P. Halstead

(57) ABSTRACT

Substituted dihydroisoxazole derivatives useful as inhibitors of β-lactamases are provided. The invention further provides medical uses of substituted dihydroisoxazole derivatives, for example, as antibacterial agents.

20 Claims, 2 Drawing Sheets

A

B

C

COMPOSITIONS AND METHODS FOR INHIBITING BETA-LACTAMASE

RELATED APPLICATIONS

This application claims the benefit of priority to U.S. Provisional Patent Application Ser. No. 62/236,228, filed Oct. 2, 2015. This application is hereby incorporated by reference in its entirety.

BACKGROUND

Bacterial resistance to antibiotics is a serious threat to modern medical care. Bacteria have a remarkable ability to develop resistance to new antibiotics rendering them quickly ineffective. For example, the widespread use of penicillins and cephalosporins has resulted in the emergence of β-lactamases, a family of bacterial enzymes that catalyze the hydrolysis of the β-lactam ring common to numerous antibiotics. Hydrolysis of the β-lactam ring leads to the inactivation of the antibiotic and allows the bacteria to resist the antibiotic. β-lactamase inhibitors deactivate or slow down the β-lactamase enzyme activity thus reducing the degradation of β-lactam antibiotics by the bacteria. The continuing evolution of antibacterial resistance could result in bacterial strains against which currently available antibacterial agents will be ineffective.

Therefore, there is a continuing need to discover and develop compounds that inhibit β-lactamases and that may be useful to treat bacterial infections.

SUMMARY OF INVENTION

In certain embodiments, the invention relates to compounds having the structure of Formula I:

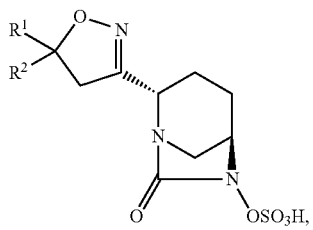

and pharmaceutically acceptable salts thereof, wherein $R^1$ and $R^2$ are as defined herein.

The invention also relates to methods for inhibiting β-lactamase, comprising contacting the β-lactamase with a compound of the invention.

The invention further relates to methods for inhibiting growth of a bacterium comprising contacting the bacterium with a β-lactam antibiotic and a compound of the invention.

The invention also relates to methods for treating a bacterial infection, comprising administering a compound of the invention to a subject in need of treatment. In certain embodiments, the method for treating a bacterial infection further comprises administering a β-lactam antibiotic.

DETAILED DESCRIPTION OF THE INVENTION

Figure 1:
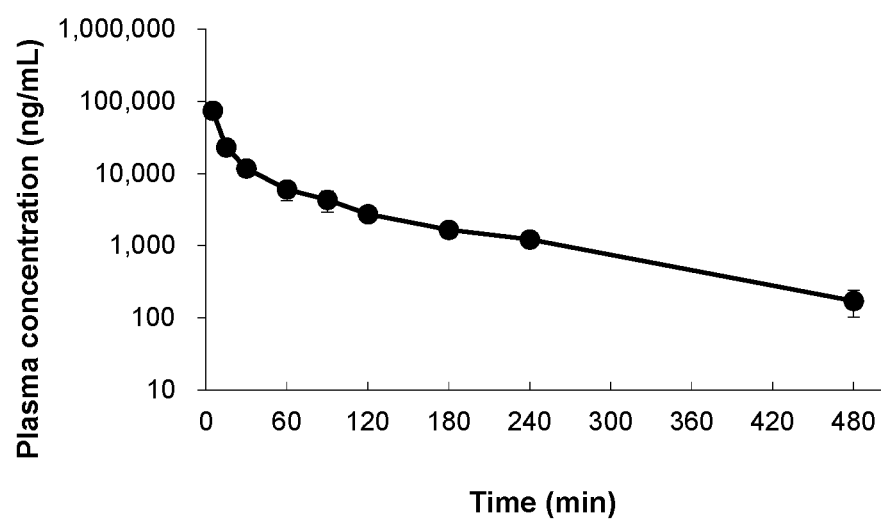
FIG. 1 includes 3 panels (Panels A-C) showing the pharmacokinetics of representative compounds of the invention. Panel A is a plot of the pharmacokinetics of the compound of Example 2. Panel B is a plot of the pharmacokinetics of the compound of Example 5. Panel C is a plot of the pharmacokinetics of the compound of Example 17.
Figure 1:
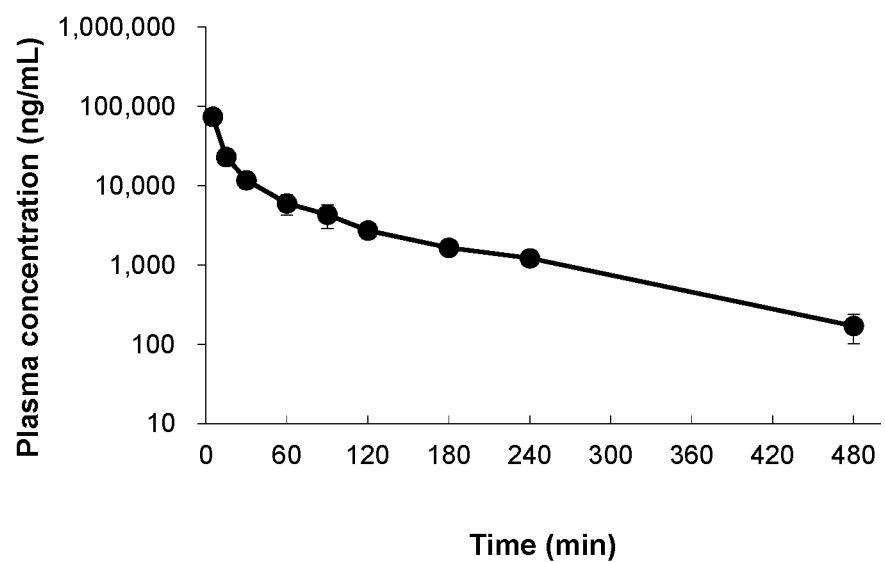
Figure 1:
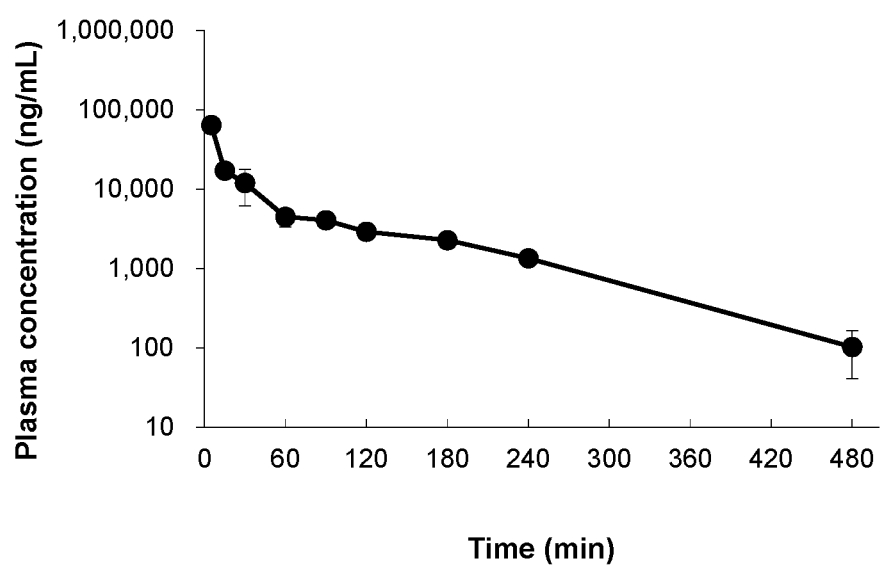

In certain aspects, the invention provides substituted dihydroisoxazole derivatives and pharmaceutical compositions thereof. In certain aspects, the compounds, and their pharmaceutically acceptable salts are inhibitors of β-lactamase. In other aspects, the compounds, and their pharmaceutically acceptable salts, are useful in combination with beta-lactam antibiotics, or alone, for inhibiting growth of a bacterium and for the treatment of a bacterial infection, including infections caused by drug resistant organisms, including multi-drug resistant organisms

I. Compounds

In certain embodiments, the invention relates to compounds having the structure of Formula I, or a pharmaceutically acceptable salt thereof:

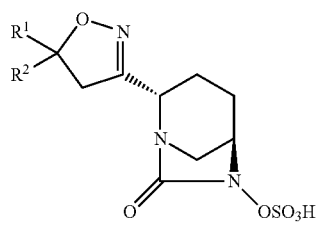

wherein $R^1$ and $R^2$ are independently selected from H, hydroxyalkyl, —C(O)—NH$_2$, amido-, amino- or guanidino substituted alkyl, amido-, amino-, or guanidino-substituted alkoxyalkyl, and —(CH$_2$)$_p$—O—NHR$^3$, or $R^1$ and $R^2$ combine to form an amino- or guanidino-substituted cycloalkyl ring, or an optionally substituted nitrogen-containing heterocyclyl ring;

p is an integer from 1 to 6; and $R^3$ is, independently for each occurrence, selected from H, lower alkyl, and —C(=NH)NH$_2$.

In certain embodiments, at least one of $R^1$ and $R^2$ is independently selected from

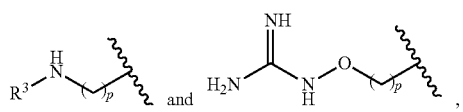

wherein p is an integer from 1 to 5. In certain such embodiments, both $R_1$ and $R_2$ are independently selected from this list, while in other such embodiments, the other of $R_1$ and $R_2$ is H.

In certain embodiments, p is independently an integer from 1 to 5, from 1 to 4, from 2 to 5, from 1 to 3, from 2 to 4, or from 2 to 3.

In certain embodiments, $R^1$ and $R^2$ combine to form a structure of Formula A

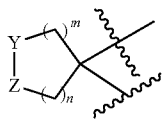

wherein

Y and Z are each independently $CHR^4$, $NR^5$, or absent;

$R^4$ is, independently for each occurrence, selected from H, amido-, amino-, or guanidino-substituted lower alkyl, and $NHR^3$;

$R^5$ is, independently for each occurrence, selected from H, amido-, amino-, or guanidino-substituted lower alkyl, and —C(=NH)NH$_2$; and m and n are each independently an integer from 1 to 3; provided that both Y and Z are not absent.

In certain embodiments, the compound has the structure of formula II or a pharmaceutically acceptable salt thereof:

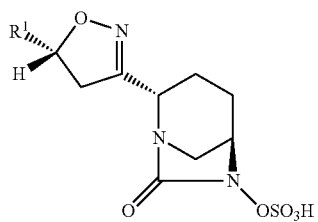

wherein $R^1$ is an amido-, amino- or guanidino substituted alkyl, an amido-, amino-, guanidino-substituted alkoxyalkyl, or —(CH$_2$)$_p$—O—NHR$^3$, and $R^3$ is as defined for Formula I.

In certain embodiments, the compound has the structure of formula III or a pharmaceutically acceptable salt thereof:

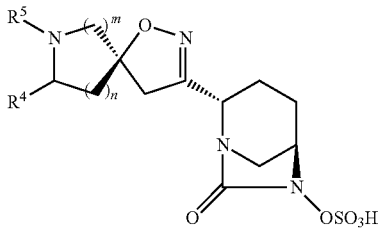

wherein $R^4$ and $R^5$ are as defined for Formula I and m is less than or equal to n.

In certain embodiments, the compound is selected from [(2S,5R)-2-[5-(2-aminoethyl)-4,5-dihydroisoxazol-3-yl]-7-oxo-1,6-diazabicyclo[3.2.1]octan-6-yl]hydrogen sulfate, [(2S, 5R)-2-[5-(aminomethyl)-4,5-dihydroisoxazol-3-yl]-7-oxo-1,6-diazabicyclo[3.2.1]octan-6-yl]hydrogen sulfate, [(2S, 5R)-2-[5-(3-aminopropyl)-4,5-dihydroisoxazol-3-yl]-7-oxo-1,6-diazabicyclo[3.2.1]octan-6-yl]hydrogen sulfate, [(2S,5R)-2-[5-(guanidinooxymethyl)-4,5-dihydroisoxazol-3-yl]-7-oxo-1,6-diazabicyclo[3.2.1]octan-6-yl]hydrogen sulfate, [(2S, 5R)-2-[5,5-bis(aminomethyl)-4H-isoxazol-3-yl]-7-oxo-1,6-diazabicyclo[3.2.1]octan-6-yl]hydrogen sulfate, [(2S, 5R)-2-(1-oxa-2,7,8-triazaspiro[4.4]non-2-en-3-yl)-7-oxo-1,6-diazabicyclo[3.2.1]octan-6-yl]hydrogen sulfate, [(2S, 5R)-2-(5-oxa-2,6-diazaspiro[3.4]oct-6-en-7-yl)-7-oxo-1,6-diazabicyclo[3.2.1]octan-6-yl]hydrogen sulfate, [(2S, 5R)-2-(2-amino-5-oxa-6-azaspiro[3.4]oct-6-en-7-yl)-7-oxo-1,6-diazabicyclo[3.2.1]octan-6-yl]hydrogen sulfate, [(2S, 5R)-2-(1-oxa-2,7-diazaspiro[4.4]non-2-en-3-yl)-7-oxo-1,6-diazabicyclo[3.2.1]octan-6-yl]hydrogen sulfate, [(2S, 5R)-2-(1-oxa-2,8-diazaspiro[4.5]dec-2-en-3-yl)-7-oxo-1,6-diazabicyclo[3.2.1]octan-6-yl]hydrogen sulfate, [(2S,5R)-2-(8-carbamimidoyl-1-oxa-2,8-diazaspiro[4.5]dec-2-en-3-yl)-7-oxo-1,6-diazabicyclo[3.2.1]octan-6-yl]hydrogen sulfate, [(2S,5R)-2-[7-(2-amino-2-oxo-ethyl)-1-oxa-2,7-diazaspiro[4.4]non-2-en-3-yl]-7-oxo-1,6-diazabicyclo[3.2.1]octan-6-yl]hydrogen sulfate, [(2S,5R)-2-[5-(aminomethyl)-5-(hydroxymethyl)-4H-isoxazol-3-yl]-7-oxo-1,6-diazabicyclo[3.2.1]octan-6-yl]hydrogen sulfate, [(2S,5R)-2-[5-(aminomethyl)-5-carbamoyl-4H-isoxazol-3-yl]-7-oxo-1,6-diazabicyclo[3.2.1]octan-6-yl]hydrogen sulfate, [(2S)-2-[(5R)-5-(aminomethyl)-4,5-dihydroisoxazol-3-yl]-7-oxo-1,6-diazabicyclo[3.2.1]octan-6-yl]hydrogen sulfate, [(2S)-2-[(5S)-5-(aminomethyl)-4,5-dihydroisoxazol-3-yl]-7-oxo-1,6-diazabicyclo[3.2.1]octan-6-yl]hydrogen sulfate, [(2S,5R)-2-[(5R)-1-oxa-2,7-diazaspiro[4.4]non-2-en-3-yl]-7-oxo-1,6-diazabicyclo[3.2.1]octan-6-yl] hydrogen sulfate, [(2S,5R)-2-[(5S)-1-oxa-2,7-diazaspiro[4.4]non-2-en-3-yl]-7-oxo-1,6-diazabicyclo[3.2.1]octan-6-yl]hydrogen sulfate or a pharmaceutically acceptable salt thereof.

In certain embodiments, compounds of the invention may be racemic. In certain embodiments, compounds of the invention may be enriched in one enantiomer. For example, a compound of the invention may have greater than 30% ee, 40% ee, 50% ee, 60% ee, 70% ee, 80% ee, 90% ee, or even 95% or greater ee. The compounds of the invention have more than one stereocenter. Consequently, compounds of the invention may be enriched in one or more diastereomer. For example, a compound of the invention may have greater than 30% de, 40% de, 50% de, 60% de, 70% de, 80% de, 90% de, or even 95% or greater de.

This invention includes the use of pharmaceutically acceptable salts of compounds of the invention in the compositions and methods of the present invention. The term "pharmaceutically acceptable salt" as used herein includes salts derived from inorganic or organic acids including, for example, hydrochloric, hydrobromic, sulfuric, nitric, perchloric, phosphoric, formic, acetic, lactic, maleic, fumaric, succinic, tartaric, glycolic, salicylic, citric, methanesulfonic, benzenesulfonic, benzoic, malonic, trifluoroacetic, trichloroacetic, naphthalene-2-sulfonic, and other acids. Pharmaceutically acceptable salt forms can include forms wherein the ratio of molecules comprising the salt is not 1:1. For example, the salt may comprise more than one inorganic or organic acid molecule per molecule of base, such as two hydrochloric acid molecules per molecule of compound of Formula I. As another example, the salt may comprise less than one inorganic or organic acid molecule per molecule of base, such as two molecules of compound of Formula I per molecule of tartaric acid.

In further embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to Na, Ca, K, Mg, Zn or other metal salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Exemplary compounds of Formula I are depicted in Table 1. The compounds of Table 1 may be depicted as the free base or the conjugate acid. Compounds may be isolated in either the free base form, as a salt (e.g., a sodium salt) or in both forms. In the chemical structures shown below, standard chemical abbreviations are sometimes used.

TABLE 1

Exemplary Compounds of Formula I

| Compound of | Structure |
|---|---|
| Example 1 | *(structure)* |
| Example 2 | *(structure)* |
| Example 3 | *(structure)* |
| Example 4 | *(structure)* |
| Example 5 | *(structure)* |
| Example 6 | *(structure)* |
| Example 7 | *(structure)* |
| Example 8 | *(structure)* |

TABLE 1-continued

Exemplary Compounds of Formula I

| Compound of | Structure |
|---|---|
| Example 9 | 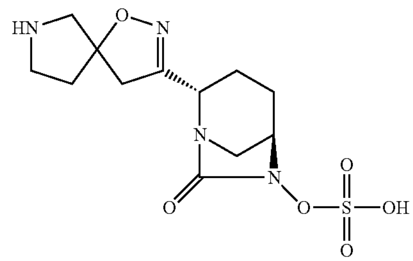 [SMILES: O=C1N2C[C@@H](CC[C@H]2C2=NOC3(CNNC3)C2)N1OS(=O)(=O)O] |
| Example 10 | 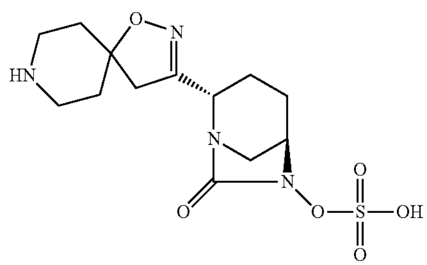 [SMILES: O=C1N2C[C@@H](CC[C@H]2C2=NOC3(CCNCC3)C2)N1OS(=O)(=O)O] |
| Example 11 | 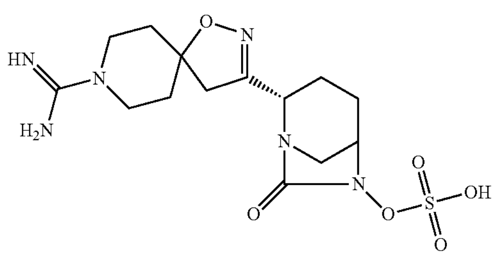 [SMILES: N=C(N)N1CCC2(CC1)CC([C@@H]1CCC3CN1C(=O)N3OS(=O)(=O)O)=NO2] |
| Example 12 | 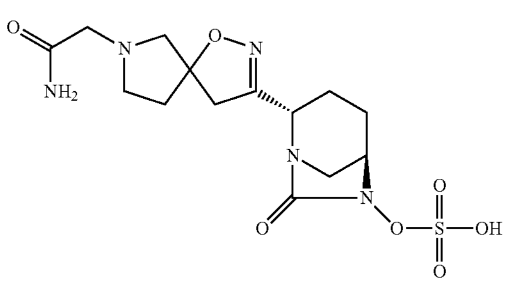 [SMILES: NC(=O)CN1CCC2(CC([C@@H]3CC[C@@H]4CN3C(=O)N4OS(=O)(=O)O)=NO2)C1] |
| Example 13 | 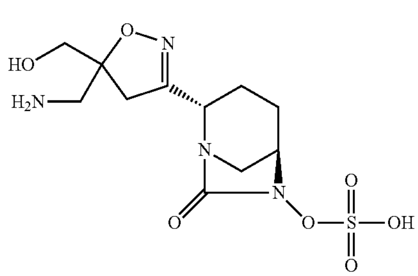 [SMILES: NCC1(CO)CC([C@@H]2CC[C@@H]3CN2C(=O)N3OS(=O)(=O)O)=NO1] |
| Example 14 | |
| Example 15 | |
| Example 16 | |
| Example 17 | |
| Example 18 | |

II. Uses of Compounds

In certain aspects, the invention provides methods for inhibiting β-lactamase, the method comprising contacting the β-lactamase with a compound of Formula I.

In certain aspects, the invention provides methods for inhibiting growth of a bacterium, the method comprising contacting the bacterium with a β-lactam antibiotic and a compound of Formula I.

In certain embodiments, the β-lactam antibiotic includes but is not limited to any antibiotic belonging, but not limited to, the classes of clavams, carbapenems, monobactams, penicillins, and or cephalosporins, or with any other compound susceptible to serine β-lactamases.

In certain embodiments, the β-lactam antibiotic is a cephalosporin. Examples of cephalosporins include, but are not limited to, Cefacetrile (cephacetrile), Cefadroxil (cefadroxyl), Cefalexin (cephalexin), Cefaloglycin (cephaloglycin), Cefalonium (cephalonium), Cefaloridine (cephaloradine), Cefalotin (cephalothin), Cefapirin (cephapirin), Cefatrizine, Cefazaflur, Cefazedone, Cefazolin (cephazolin), Cefradine (cephradine), Cefroxadine, Ceftezole, Cefaclor, Cefamandole, Cefmetazole, Cefonicid, Cefotetan, Cefoxitin, Cefprozil (cefproxil), Cefuroxime, Cefuzonam, Cefcapene, Cefdaloxime, Cefdinir, Cefditoren, Cefetamet, Cefixime, Cefmenoxime, Cefodizime, Cefotaxime, Cefpimizole, Cefpodoxime, Cefteram, Ceftibuten, Ceftiofur, Ceftiolene, Ceftizoxime, Ceftriaxone, Cefoperazone, Ceftazidime, Cefclidine, Cefepime, Cefluprenam, Cefoselis, Cefozopran, Cefpirome, Cefquinome, Cefaclomezine, Cefaloram, Cefaparole, Cefcanel, Cefedrolor, Cefempidone, Cefetrizole, Cefivitril, Cefmatilen, Cefmepidium, Cefovecin, Cefoxazole, Cefrotil, Cefsumide, Ceftaroline, Ceftioxide, Cefuracetime, cefbuperazone, cefminox, ceforanide, cefotiam, cefpiramide, cefsulodin, ceftobiprole latamoxef, loracarbef and Ceftolozane. In one embodiment the cephalosporin is Ceftolozane or Ceftazidime.

In certain embodiment, the β-lactam antibiotic is a carbapenem. Examples of carbapenem antibiotics include, but are not limited to, Imipenem, Imipenem/Cilastatin, Biapenem, Doripenem, Meropenem, Ertapenem and Panipenem. In one embodiment the Carbapenem is Imipenem/Cilastatin or Meropenem.

In certain embodiment of the invention, the β-lactam antibiotic is a monobactam. Examples of monobactam antibiotics include, but are not limited to Aztreonam, Tigemonam, Carumonam, BAL30072 and Nocardicin A.

In certain embodiment of the invention, the β-lactam antibiotic is a penem. In one embodiment of the invention, the β-lactam antibiotic is a penicillin. Examples of penicillin antibiotics include, but are not limited to Amoxicillin, Ampicillin, Azlocillin, Mezlocillin, Apalcillin, Hetacillin, Becampicillin, Carbenicillin, Sulbenicillin, Ticarcillin, Piperacillin, Azlocillin, Mecillinam, Pivmecillinam, Methicillin, Ciclacillin, Talampicillin, Aspoxicillin, Oxacillin, Cloxacillin, Dicloxacillin, Flucloxacillin, Nafcillin and Pivampicillin.

In certain aspects, the invention provides methods for treating a bacterial infection, comprising administering a compound of Formula I to a subject in need of treatment.

In one aspect, bacterial infection may refer to an infection of any organ or tissue in the body caused by β-lactam resistant bacteria, preferably, Gram-negative β-lactam resistant bacteria. These organs or tissue include, without limitation, skeletal muscle, skin, bloodstream, kidneys, heart, lung and bone. For example, a compound of the invention in conjunction with a β-lactam antibiotic, can be administered to a subject to treat, without limitation, skin and soft tissue infections (e.g., complex skin infections), bacteremia, intra-abdominal infections and urinary tract infections (e.g., UTI). In addition, a compound of the invention may be used to treat community acquired respiratory infections, including, without limitation, otitis media, sinusitis, chronic bronchitis and pneumonia (including community-acquired pneumonia, hospital-acquired pneumonia and ventilator associated pneumonia), including pneumonia caused by drug-resistant *Pseudomonas aeruginosa*. In certain embodiments, a compound of the invention in conjunction with a β-lactam antibiotic, can be administered to a subject to treat mixed infections that comprise different types of Gram-negative bacteria, or which comprise both Gram-positive and Gram-negative bacteria. These types of infections include intra-abdominal infections and obstetrical/gynecological infections. In certain embodiments, a compound of the invention in conjunction with a β-lactam antibiotic, may also be administered to a subject to treat an infection including, without limitation, endocarditis, nephritis, septic arthritis, intra-abdominal sepsis, bone and joint infections and osteomyelitis. In certain embodiments, a compound of the invention in conjunction with a β-lactam antibiotic may also be directly injected or administered into an abscess, ventricle or joint.

In some embodiments, the infection may be a gynecological infection, a respiratory tract infection (RTI), a sexually transmitted disease, syphilis, a urinary tract infection, an acute exacerbation of chronic bronchitis (ACEB), acute otitis media, acute sinusitis, an infection caused by drug resistant bacteria, sepsis, catheter-related sepsis, chancroid, *chlamydia*, community-acquired pneumonia (CAP), a complicated skin and skin structure infection, a uncomplicated skin and skin structure infection, endocarditis, febrile neutropenia, gonococcal cervicitis, gonococcal urethritis, hospital-acquired pneumonia (HAP), osteomyelitis, or an intra-abdominal infection (IAI).

In certain embodiments, bacterial infection may refer to an infection caused by Gram-negative bacteria, also referred to as a "Gram-negative infection." In one aspect, the Gram-negative infection is an infection resistant to one or more antibiotics. In one aspect, the Gram-negative infection is a multi-drug resistant infection. Representative Gram-negative pathogens known to express β-lactamases include, but are not limited to *Acinetobacter* spp. (including *Acinetobacter baumannii*), *Citrobacter* spp., *Escherichia* spp. (including *Escherichia coli*), *Haemophilus influenzae*, *Morganella morganii*, *Pseudomonas aeruginosa*, *Klebsiella* spp. (including *Klebsiella pneumoniae*), *Enterobacter* spp. (including *Enterobacter cloacae* and *Enterobacter aerogenes*), *Pasteurella* spp., *Proteus* spp. (including *Proteus mirabilis*), *Serratia* spp. (including *Serratia marcescens*), and *Providencia* spp. Bacterial infections can be caused or exacerbated by Gram-negative bacteria including strains which express β-lactamases that may confer resistance to penicillins, cephalosporins, monobactams and/or carbapenems.

In one embodiment of the invention is a method of treating one or more of the infections listed above comprising administering to a subject suffering from a bacterial infection an effective amount of a compound of Formula I or a pharmaceutically acceptable salt thereof, in combination with an additional antibiotic agent. In certain embodiments, the additional antibiotic agent is a β-lactam antibiotic. In one aspect, the additional antibiotic agent is a penicillin-binding protein inhibitor.

In another aspect of the invention, the compound of Formula I is administered in combination with a β-lactam antibiotic and an additional antibiotic and/or an additional β-lactamase inhibitor. In one aspect of the invention, the additional antibiotic agent is selected from one of the classes of aminoglycosides, spectinomycins, macrolides, ketolides, streptogramins, oxazolidinones, tetracyclines, fluoroquinolones, coumarin antibiotics, glycopeptides, lipoglycopeptides, nitroimidazoles, ansamycins, phenicols, mupirocyn, fosfomycin, tobramycin, linezolid, daptomycin, and vancomycin.

In one aspect of the invention, the compound of Formula I is administered in combination with a β-lactam antibiotic and a second agent which is designed to address β-lactam resistance. In one aspect of the invention, the compound of Formula I is administered in combination with a β-lactam antibiotic and a second serine beta-lactamase inhibitor. In one aspect of the invention, the second beta-lactamase inhibitor is selected from sulbactam, tazobactam, avibactam, clavulanic acid, LK-157, LK-176, SA-1-204, SA-2-13, BLI-489 (Pfizer/Wyeth), BAL0029880 and MK7655. In another aspect of the invention, the second agent designed to address β-lactam resistance may be a metallo-β-lactamase (MBL) inhibitor, also known as a Class B inhibitor.

In certain embodiments, the subject is a mammal, e.g., a human.

In certain embodiments, the β-lactamase inhibitor and β-lactam antibiotic are administered simultaneously. In alternative embodiments, the one or more additional β-lactam antibiotics are administered within about 5 minutes to within about 168 hours prior to or after administration of the β-lactamase inhibitor.

III. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

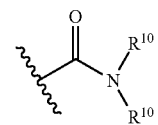

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

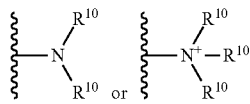

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

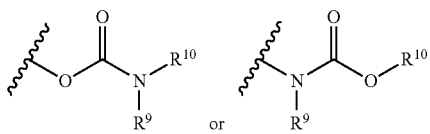

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —$OCO_2$—$R^{10}$, wherein $R^{10}$ represents a hydrocarbyl group.

The term "carboxy", as used herein, refers to a group represented by the formula —$CO_2H$.

The term "ester", as used herein, refers to a group —$C(O)OR^{10}$ wherein $R^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like. Heterocyclyl groups can also be substituted by oxo groups. For example, "heterocyclyl" encompasses both pyrrolidine and pyrrolidinone.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

As used herein, the term "oxo" refers to a carbonyl group. When an oxo substituent occurs on an otherwise saturated group, such as with an oxo-substituted cycloalkyl group (e.g., 3-oxo-cyclobutyl), the substituted group is still intended to be a saturated group. When a group is referred to as being substituted by an "oxo" group, this can mean that a carbonyl moiety (i.e., —C(=O)—) replaces a methylene unit (i.e., —CH$_2$—).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

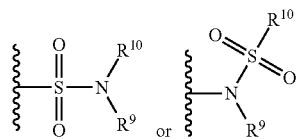

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof.

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

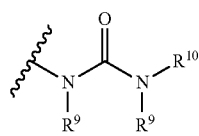

wherein $R^9$ and $R^{10}$ independently represent hydrogen or a hydrocarbyl, such as alkyl, or either occurrence of $R^9$ taken together with $R^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "prodrug" is intended to encompass compounds which, under physiologic conditions, are converted into the therapeutically active agents of the present invention (e.g., a compound of formula I). A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of formula I in a formulation represented above can be replaced with the corresponding suitable prodrug, e.g., wherein a hydroxyl in the parent compound is presented as an ester or a carbonate or carboxylic acid present in the parent compound is presented as an ester.

EXAMPLES

Examples of compounds of Formula I or pharmaceutically acceptable salts thereof are listed above in Table 1. The ability of compounds Formula I or pharmaceutically acceptable salts thereof to inhibit growth of a bacterium was established with the representative compounds of Formula I listed in Tables 1 and 2 using the assays described below.

A. Chemical Syntheses

The general procedures used in the methods to prepare the compounds of the present invention are outlined in Schemes 1 and 2 and are described below.

Scheme 1

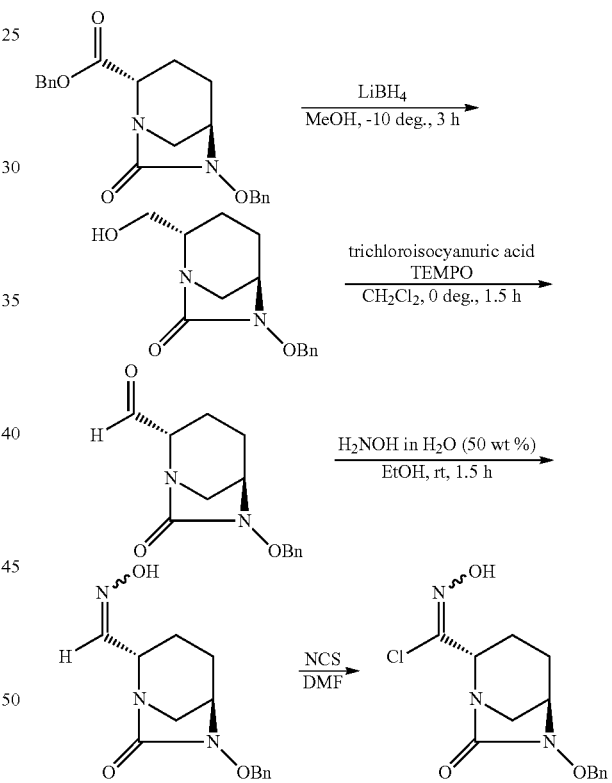

Scheme 2

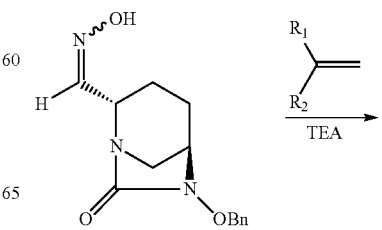

19
-continued
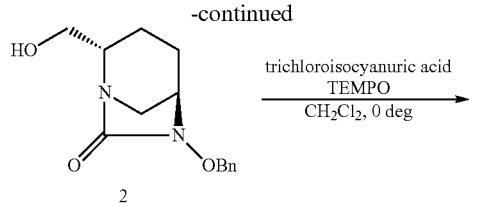
1) Pd/C, MeOH
2) SO₃—Pyr
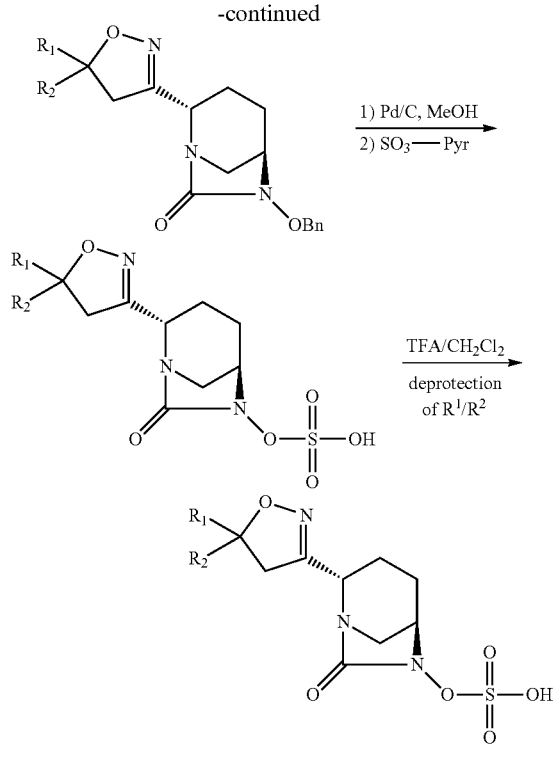
TFA/CH₂Cl₂
deprotection of R¹/R²
Example 1
[(2S,5R)-2-[5-(2-aminoethyl)-4,5-dihydroisoxazol-3-yl]-7-oxo-1,6-diazabicyclo[3.2.1]octan-6-yl]hydrogen sulfate
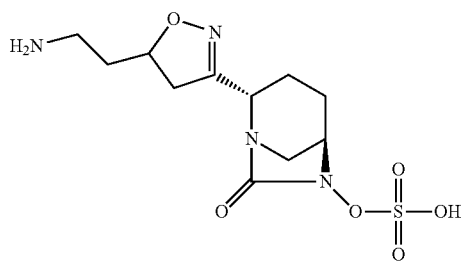 [SMILES: NCCC1CC([C@@H]2CC[C@@H]3CN2C(=O)N3OS(=O)(=O)O)=NO1]
The synthesis of [(2S,5R)-2-[5-(2-aminoethyl)-4,5-dihydroisoxazol-3-yl]-7-oxo-1,6-diazabicyclo[3.2.1]octan-6-yl] hydrogen sulfate is carried out according to Scheme 3 and as outlined in the steps below.
Scheme 3
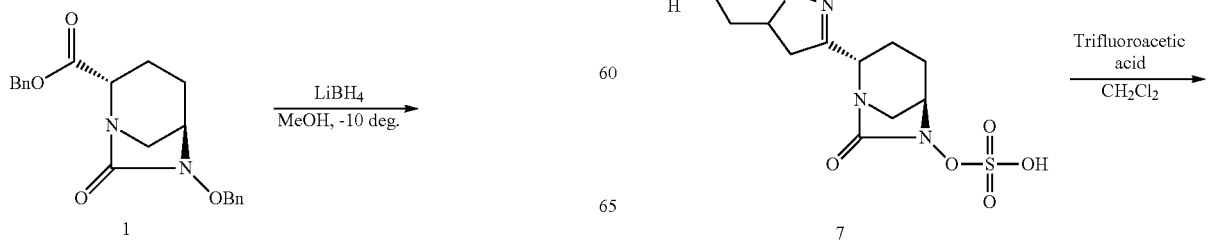
20
-continued -continued

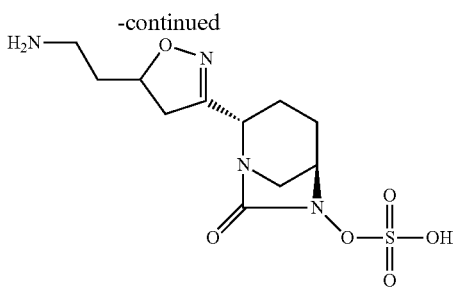

Example 1

Step 1: (2S, 5R)-6-benzyloxy-2-(hydroxymethyl)-1,6-diazabicyclo[3.2.1]octan-7-one

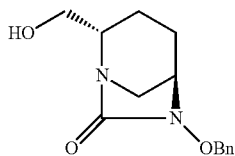

2

To a solution of (2S, 5R)-benzyl 6-(benzyloxy)-7-oxo-1,6-diazabicyclo[3.2.1]octane-2-carboxylate (10 g, 27.3 mmol) in MeOH (70 mL) was added 2.0 M solution of LiBH$_4$ in THF (20.5 mL, 40.9 mmol) was added at −10° C. After 10 minutes, another portion of 2.0 M solution of LiBH$_4$ (20.5 mL, 40.9 mmol) in THF was added and the mixture was stirred for 2 h at −10° C. to 0° C. The reaction mixture was carefully quenched by addition of saturated NaH$_2$PO$_4$ solution (100 mL) at 0° C. The reaction mixture was diluted with water and extracted with methylene chloride (250 mL×3). The combined organic layer was concentrated and purified by silica gel column chromatography (50-100% EtOAc/n-Hexane) to give Compound-2 (5.8 g, 81%).

$^1$H NMR (400 MHz, CDCl$_3$) δ 7.46-7.37 (m, 5H), 5.07 (d, J=11.6 Hz, 1H), 4.92 (d, J=11.6 Hz, 1H), 3.73 (br, 1H), 3.62-3.57 (m, 2H), 3.35 (m, 1H), 3.01 (d, J=11.6 Hz, 1H), 2.93 (br d, J=11.6 Hz, 1H) 2.23 (br, 1H), 2.07-1.93 (m, 2H), 1.57-1.35 (m, 2H).

Step 2: (2S, 5R)-6-benzyloxy-7-oxo-1,6-diazabicyclo[3.2.1]octane-2-carbaldehyde

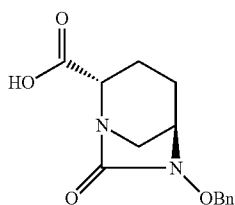

3

To a solution of Compound-2 (5 g, 19.1 mmol) was added TEMPO (0.3 g, 1.9 mmol) and trichloroisocyanuric acid (5.3 g, 22.8 mmol) in methylene chloride (100 mL) at 0° C. The mixture was stirred for 2 h at 0° C., and filtered through celite. The mixture was washed with saturated NaHCO$_3$ (200 mL) and brine (50 mL), dried over anhydrous sodium sulfate, and concentrated under reduced pressure to give Compound-3 as a yellow oil with quantitative yield.

$^1$H NMR (400 MHz, CDCl$_3$) δ 9.74 (s, 1H), 7.44-7.37 (m, 5H), 5.07 (d, J=11.6 Hz, 1H), 4.90 (d, J=11.6 Hz, 1H), 3.85 (d, J=8.0 Hz, 1H), 3.28 (br, 1H), 3.14 (d, J=13.2 Hz, 1H), 2.56 (d, J=11.6 Hz, 1H), 2.20-1.91 (m, 3H), 1.46 (m, 1H).

Step 3: (2S, 5R)-6-benzyloxy-7-oxo-1,6-diazabicyclo[3.2.1]octane-2-carbaldehyde oxime

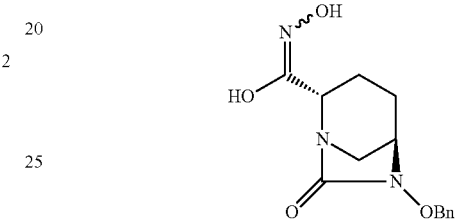

4

To a solution of Compound-3 (19.1 mmol) in EtOH (50 mL) was added Hydroxylamine (1.25 mL, 19.1 mmol, 50% aq. Sol.) at 0° C. The reaction mixture was stirred for 1 h at 0° C. and concentrated under reduced pressure to give Compound-4 as a light yellow foam with quantitative yield.

Step 4: (2S, 5R)-6-benzyloxy-N-hydroxy-7-oxo-1,6-diazabicyclo[3.2.1]octane-2-carboximidoyl chloride

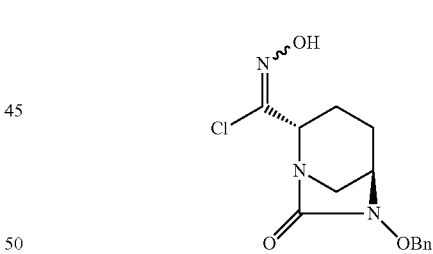

5

To a solution of Compound-4 (0.3 g, 1.09 mmol) in DMF (5 mL) was added (N-chlorosuccinimide (0.15 g, 1.14 mmol) at room temperature. After stirring for 1 h at room temperature, the reaction mixture was diluted with EA (20 mL), washed with water (20 mL) twice, dried over anhydrous sodium sulfate, and concentrated under reduced pressure to give a light yellow foam with quantitative yield.

$^1$H NMR (400 MHz, CDCl$_3$) δ 7.67 (s, 1H), 7.44-7.35 (m, 5H), 5.07 (d, J=12.0 Hz, 1H), 4.92 (d, J=12.0 Hz, 1H), 4.24 (d, J=6.0 Hz, 1H), 3.34 (bs, 1H), 2.97 (d, J=12.0 Hz, 1H), 2.87 (d, J=12.0 Hz, 1H), 2.14-2.01 (m, 3H), 1.75 (m, 1H).

Step 5: tert-butyl N-[2-[3-[(2S, 5R)-6-benzyloxy-7-oxo-1,6-diazabicyclo[3.2.1]octan-2-yl]-4, 5-dihydroisoxazol-5-yl]ethyl]carbamate

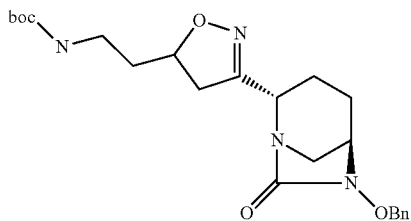

To a solution of Compound-5 (1.09 mmol) and tert-Butyl but-3-enylcarbamate (0.72 g, 4.2 mmol) in methylene chloride (10 mL) was added TEA (0.18 mL, 1.3 mmol) drop-wisely at room temperature. The mixture was stirred overnight at room temperature. The mixture was washed with saturated NaHCO₃ (10 mL) and dried over anhydrous sodium sulfate. The combined organic layer was concentrated under reduced pressure and purified by silica gel column chromatography (30% EA/Hexane) to give Compound-6 (0.23 g, 47%).

¹H NMR (400 MHz, DMSO-d₆) δ 7.46-7.36 (m, 5H), 6.87 (m, 1H), 4.97-4.91 (m, 2H), 4.56 (m, 1H), 4.05 (d, J=6.40 Hz, 1H), 3.67 (m, 1H), 3.09-2.82 (m, 4H), 2.75-2.57 (m, 1H), 2.00 (m, 1H), 1.86-1.61 (m, 5H), 1.37 (s, 9H).

Step 6: tert-butyl N-[2-[3-[(2S, 5R)-7-oxo-6-sulfooxy-1,6-diazabicyclo[3.2.1]octan-2-yl]-4,5-dihydroisoxazol-5-yl]ethyl]carbamate

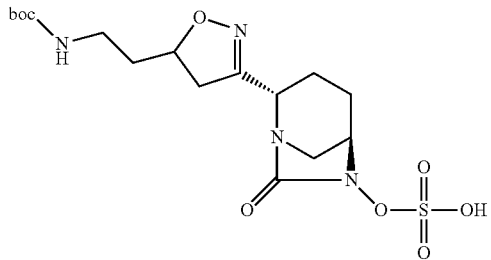

To a solution of Compound-6 (0.23 g, 0.52 mmol) in EtOH/EA (4 mL/4 mL) was added Pd/C (0.1 g). The reaction mixture was stirred for 1 h under hydrogen atmosphere. The mixture was filtered through Celite®. The filtrate was washed with Ethyl Acetate (4 mL) and concentrated under reduced pressure. The resulting intermediate was used without purification for next step.

To a solution of crude intermediate in pyridine (2 mL) was added SO₃.Pyr (0.41 g, 2.6 mmol). The reaction mixture was stirred overnight at room temperature. The resulting mixture was filtered, concentrated and purified by silica gel column chromatography (5% MeOH/MC) to give Compound-7 (0.15 g, 66%).

¹H NMR (400 MHz, DMSO-d₆) δ 4.56 (m, 1H), 4.03 (d, J=6.8 Hz, 1H), 4.00 (br, 1H), 3.11-2.91 (m, 4H), 2.78-2.62 (m, 2H), 2.00-1.86 (m, 2H), 1.83-1.61 (m, 4H), 1.37 (s, 9H).

Step 7: [(2S, 5R)-2-[5-(2-aminoethyl)-4,5-dihydroisoxazol-3-yl]-7-oxo-1,6-diazabicyclo[3.2.1]octan-6-yl]hydrogen sulfate To a solution of Compound-7 (0.15 g, 0.35 mmol) in methylene chloride (2 mL) was added trifluoroacetic acid (1 mL) at 0° C. After stirring for 1 h at room temperature, the reaction mixture was diluted with diethyl ether (6 mL) and stirred for an additional 0.5 h at room temperature. The resulting precipitate was collected by filtration to give Example 1 (0.10 g, 85%) as a white solid.

¹H NMR (400 MHz, DMSO-d₆) δ 7.70 (br, 3H), 4.69 (m, 1H), 4.09 (m, 1H), 4.03 (br, 1H), 3.15 (dd, J=17.6, 10.8 Hz, 1H), 2.97-2.86 (m, 3H), 2.77-2.71 (m, 2H), 2.02-1.68 (m, 6H).

Example 2

[(2S, 5R)-2-[5-(aminomethyl)-4,5-dihydroisoxazol-3-yl]-7-oxo-1,6-diazabicyclo[3.2.1]octan-6-yl]hydrogen sulfate

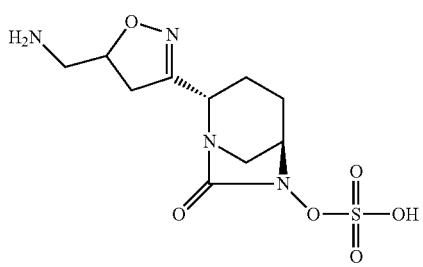

[(2S, 5R)-2-[5-(aminomethyl)-4,5-dihydroisoxazol-3-yl]-7-oxo-1,6-diazabicyclo[3.2.1]octan-6-yl]hydrogen sulfate was prepared by following steps 5-7 in Example 1 using tert-butyl N-allylcarbamate for the olefin.

¹H NMR (400 MHz, DMSO-d₆) δ 7.97 (br, 2H), 7.92 (br, 1H), 4.81 (m, 1H), 4.09 (br, 1H), 4.03 (br, 1H), 3.21 (m, 1H), 2.97-2.72 (m, 5H), 2.03-1.65 (m, 4H).

Example 3

[(2S, 5R)-2-[5-(3-aminopropyl)-4,5-dihydroisoxazol-3-yl]-7-oxo-1,6-diazabicyclo[3.2.1]octan-6-yl]hydrogen sulfate

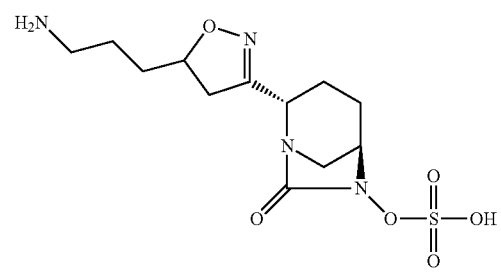

[(2S, 5R)-2-[5-(3-aminopropyl)-4,5-dihydroisoxazol-3-yl]-7-oxo-1,6-diazabicyclo[3.2.1]octan-6-yl]hydrogen sulfate was prepared following steps 5-7 in Example 1 using, tert-butyl N-pent-4-enylcarbamate for the olefin.

¹H NMR (400 MHz, DMSO-d₆) δ 7.66 (br, 3H), 4.62 (m, 1H), 4.07-4.12 (m, 2H), 3.12 (m, 1H), 2.95 (m, 1H), 2.82-2.60 (m, 4H), 2.02-1.88 (m, 2H), 1.79-1.58 (m, 6H).

Example 4

[(2S,5R)-2-[5-(guanidinooxymethyl)-4,5-dihydroisoxazol-3-yl]-7-oxo-1,6-diazabicyclo[3.2.1]octan-6-yl]hydrogen sulfate

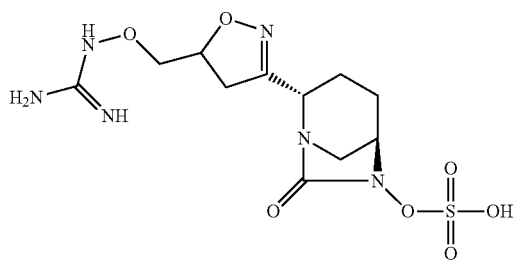 [SMILES: N=C(N)NOCC1CC([C@@H]2CC[C@@H]3CN2C(=O)N3OS(=O)(=O)O)=NO1]

[(2S,5R)-2-[5-(guanidinooxymethyl)-4, 5-dihydroisoxazol-3-yl]-7-oxo-1,6-diazabicyclo[3.2.1]octan-6-yl]hydrogen sulfate is prepared following steps 5-7 in Example 1 using tert-butyl N-allylcarbamate for the olefin.

¹H NMR (400 MHz, DMSO-d₆) δ 7.64 (br, 3H), 4.88 (m, 1H), 4.07 (d, J=6.4 Hz, 1H), 4.01 (br, 1H), 3.92-3.83 (m, 2H), 3.12 (m, 1H), 2.95-2.83 (m, 2H), 2.75 (d, J=15.6 Hz, 1H), 2.02-1.69 (m, 4H).

Example 5

[(2S, 5R)-2-[5,5-bis(aminomethyl)-4H-isoxazol-3-yl]-7-oxo-1,6-diazabicyclo[3.2.1]octan-6-yl]hydrogen sulfate

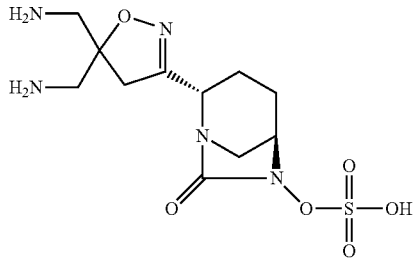 [SMILES: NCC1(CN)CC([C@@H]2CC[C@@H]3CN2C(=O)N3OS(=O)(=O)O)=NO1]

[(2S, 5R)-2-[5,5-bis(aminomethyl)-4H-isoxazol-3-yl]-7-oxo-1,6-diazabicyclo[3.2.1]octan-6-yl]hydrogen sulfate was prepared following steps 5-7 in Example 1 using tert-butyl N-[2-[(tert-butoxycarbonylamino)methyl]allyl]carbamate for the olefin.

¹H NMR (400 MHz, DMSO-d₆) δ 8.13 (br, 3H), 8.03 (br, 3H), 4.14 (d, J=6.8 Hz, 1H), 4.03 (m, 1H), 3.28-3.07 (m, 6H), 2.95-2.83 (m, 2H), 2.03-1.66 (m, 4H).

Example 6

[(2S, 5R)-2-(1-oxa-2,7,8-triazaspiro[4.4]non-2-en-3-yl)-7-oxo-1,6-diazabicyclo[3.2.1]octan-6-yl]hydrogen sulfate

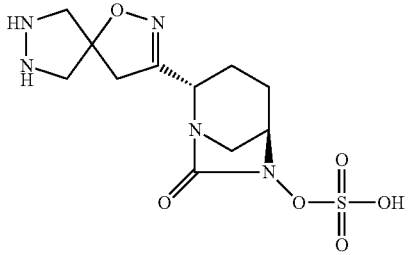 [SMILES: O=C1N2C[C@@H](CC[C@H]2C2=NOC3(CNNC3)C2)N1OS(=O)(=O)O]

[(2S, 5R)-2-(1-oxa-2,7,8-triazaspiro[4.4]non-2-en-3-yl)-7-oxo-1,6-diazabicyclo[3.2.1]octan-6-yl]hydrogen sulfate was prepared following steps 5-7 in Example 1, using ditert-butyl 4-methylenepyrazolidine-1,2-dicarboxylate for the olefin.

¹H NMR (400 MHz, DMSO-d₆) δ 4.10 (d, J=6.8 Hz, 1H), 4.01 (br, 1H), 3.50-3.22 (m, 6H), 2.99-2.77 (m, 2H), 2.02-1.68 (m, 4H).

Example 7

[(2S, 5R)-2-(5-oxa-2,6-diazaspiro[3.4]oct-6-en-7-yl)-7-oxo-1,6-diazabicyclo[3.2.1]octan-6-yl]hydrogen sulfate

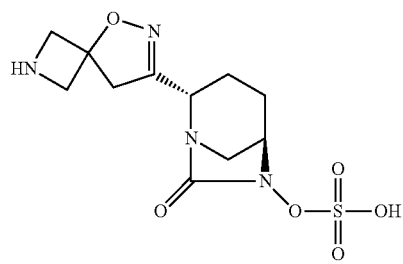 [SMILES: O=C1N2C[C@@H](CC[C@H]2C2=NOC3(CNC3)C2)N1OS(=O)(=O)O]

[(2S, 5R)-2-(5-oxa-2,6-diazaspiro[3.4]oct-6-en-7-yl)-7-oxo-1,6-diazabicyclo[3.2.1]octan-6-yl]hydrogen sulfate was prepared following steps 5-7 in Example 1, using tert-butyl 3-methyleneazetidine-1-carboxylate for the olefin.

¹H NMR (400 MHz, DMSO-d₆) δ 8.85 (br, 1H), 8.62 (br, 1H), 4.31-4.13 (m, 4H), 4.05 (d, J=7.6 Hz, 1H), 3.99 (m, 1H), 3.37 (s, 2H), 2.95-2.72 (m, 2H), 1.97-1.50 (m, 4H).

Example 8

[(2S, 5R)-2-(2-amino-5-oxa-6-azaspiro[3.4]oct-6-en-7-yl)-7-oxo-1,6-diazabicyclo[3.2.1]octan-6-yl]hydrogen sulfate

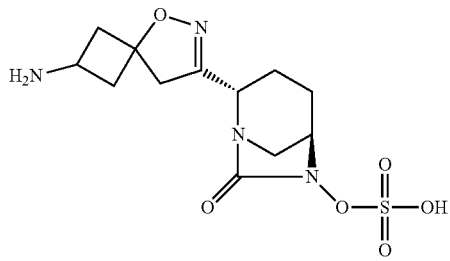 [SMILES: NC1CC2(CC([C@@H]3CC[C@@H]4CN3C(=O)N4OS(=O)(=O)O)=NO2)C1]

[(2S, 5R)-2-(2-amino-5-oxa-6-azaspiro[3.4]oct-6-en-7-yl)-7-oxo-1,6-diazabicyclo[3.2.1]octan-6-yl]hydrogen sulfate was prepared following steps 5-7 in Example 1 using tert-butyl N-(3-methylenecyclobutyl)carbamate for the olefin.

$^1$H NMR (400 MHz, DMSO-$d_6$) δ 8.02 (br, 3H), 4.05 (d, J=6.8 Hz, 1H), 4.01 (m, 1H), 3.78-3.11 (m, 3H), 2.96-2.54 (m, 6H), 2.03-1.66 (m, 4H).

Example 9

[(2S, 5R)-2-(1-oxa-2,7-diazaspiro[4.4]non-2-en-3-yl)-7-oxo-1,6-diazabicyclo[3.2.1]octan-6-yl]hydrogen sulfate

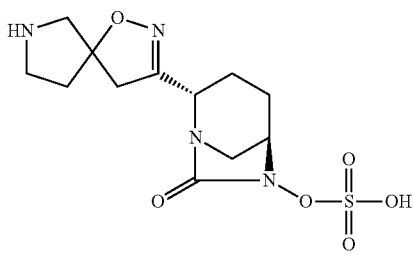 [SMILES: O=C1N2C[C@@H](CC[C@H]2C2=NOC3(CCNC3)C2)N1OS(=O)(=O)O]

[(2S, 5R)-2-(1-oxa-2,7-diazaspiro[4.4]non-2-en-3-yl)-7-oxo-1,6-diazabicyclo[3.2.1]octan-6-yl]hydrogen sulfate was prepared following steps 5-7 in Example 1 using tert-butyl 3-methylenepyrrolidine-1-carboxylate for the olefin.

$^1$H NMR (400 MHz, DMSO-$d_6$) δ 9.13 (br, 1H), 8.97 (br, 1H), 4.10 (br, 1H), 4.03 (br, 1H), 3.49-3.15 (m, 6H), 2.98-2.76 (m, 2H), 2.24-1.70 (m, 6H).

Example 10

[(2S, 5R)-2-(1-oxa-2,8-diazaspiro[4.5]dec-2-en-3-yl)-7-oxo-1,6-diazabicyclo[3.2.1]octan-6-yl]hydrogen sulfate

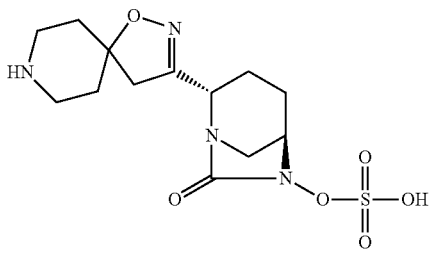 [SMILES: O=C1N2C[C@@H](CC[C@H]2C2=NOC3(CCNCC3)C2)N1OS(=O)(=O)O]

[(2S, 5R)-2-(1-oxa-2,8-diazaspiro[4.5]dec-2-en-3-yl)-7-oxo-1,6-diazabicyclo[3.2.1]octan-6-yl]hydrogen sulfate was prepared following steps 5-7 in Example 1 using tert-butyl 4-methylenepiperidine-1-carboxylate for the olefin.

$^1$H NMR (400 MHz, DMSO-$d_6$) δ 8.55 (br, 2H), 4.06 (m, 1H), 4.02 (br, 1H), 3.16 (m, 4H), 2.94 (m, 3H), 2.75 (d, 1H), 2.04-1.69 (m, 8H).

Example 11

[(2S,5R)-2-(8-carbamimidoyl-1-oxa-2,8-diazaspiro[4.5]dec-2-en-3-yl)-7-oxo-1,6-diazabicyclo[3.2.1]octan-6-yl]hydrogen sulfate

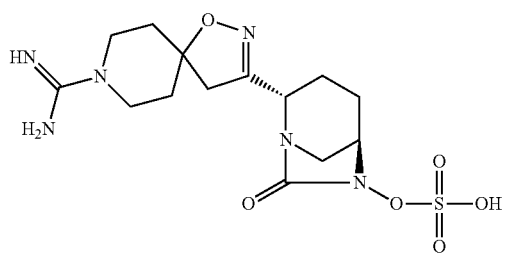 [SMILES: N=C(N)N1CCC2(CC1)CC([C@@H]1CC[C@@H]3CN1C(=O)N3OS(=O)(=O)O)=NO2]

[(2S,5R)-2-(8-carbamimidoyl-1-oxa-2,8-diazaspiro[4.5]dec-2-en-3-yl)-7-oxo-1,6-diazabicyclo[3.2.1]octan-6-yl]hydrogen sulfate was prepared following steps 5-7 in Example 1 using tert-butyl (NE)-N-[(tert-butoxycarbonylamino)-(4-methylene-1-piperidyl)methylene]carbamate for the olefin.

$^1$H NMR (400 MHz, D$_2$O) δ 4.32 (d, 1H), 4.25 (s, 1H), 3.36-3.55 (m, 4H), 3.29 (m, 1H), 3.04 (m, 3H), 2.16 (m, 2H), 1.94 (m, 6H).

Example 12

[(2S,5R)-2-[7-(2-amino-2-oxo-ethyl)-1-oxa-2,7-diazaspiro[4.4]non-2-en-3-yl]-7-oxo-1,6-diazabicyclo[3.2.1]octan-6-yl]hydrogen sulfate

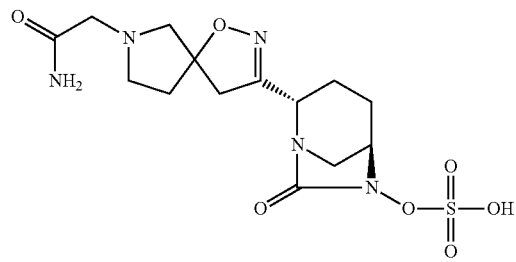 [SMILES: NC(=O)CN1CCC2(CC([C@@H]3CC[C@@H]4CN3C(=O)N4OS(=O)(=O)O)=NO2)C1]

[(2S,5R)-2-[7-(2-amino-2-oxo-ethyl)-1-oxa-2,7-diazaspiro[4.4]non-2-en-3-yl]-7-oxo-1,6-diazabicyclo[3.2.1]octan-6-yl]hydrogen sulfate was prepared following steps 5-6 in Example 1 using 2-(3-methylenepyrrolidin-1-yl)acetamide for the olefin.

$^1$H NMR (400 MHz, DMSO-$d_6$) δ 7.89 (d, J=18.0 Hz, 1H), 7.65 (d, J=18.0 Hz, 1H), 4.02 (m, 4H), 3.75 (m, 2H), 3.46-3.12 (m, 4H), 2.95 (m, 1H), 2.73 (m, 1H), 2.33 (m, 2H), 2.02-1.70 (m, 4H)

Example 13

[(2S,5R)-2-[5-(aminomethyl)-5-(hydroxymethyl)-4H-isoxazol-3-yl]-7-oxo-1,6-diazabicyclo[3.2.1]octan-6-yl]hydrogen sulfate

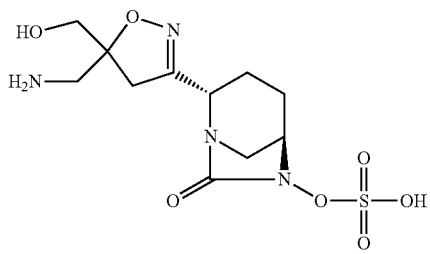 [SMILES: NCC1(CO)CC([C@@H]2CC[C@@H]3CN2C(=O)N3OS(=O)(=O)O)=NO1]

[(2S,5R)-2-[5-(aminomethyl)-5-(hydroxymethyl)-4H-isoxazol-3-yl]-7-oxo-1,6-diazabicyclo[3.2.1]octan-6-yl]hydrogen sulfate was prepared following steps 5-7 in Example 1 using tert-butyl N-[2-[[tert-butyl(dimethyl)silyl]oxymethyl]allyl]carbamate for the olefin.

$^1$H NMR (400 MHz, D$_2$O) δ 4.15 (m, 1H), 4.08 (br, 1H), 3.60 (m, 2H), 3.29-3.07 (m, 4H), 2.92 (m, 2H), 2.12-1.74 (m, 4H).

Example 14

[(2S,5R)-2-[5-(aminomethyl)-5-carbamoyl-4H-isoxazol-3-yl]-7-oxo-1,6-diazabicyclo[3.2.1]octan-6-yl]hydrogen sulfate

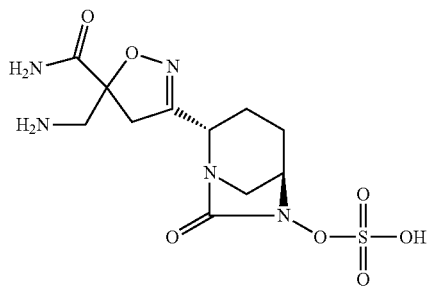 [SMILES: NCC1(C(N)=O)CC([C@@H]2CC[C@@H]3CN2C(=O)N3OS(=O)(=O)O)=NO1]

[(2S,5R)-2-[5-(aminomethyl)-5-carbamoyl-4H-isoxazol-3-yl]-7-oxo-1,6-diazabicyclo[3.2.1]octan-6-yl]hydrogen sulfate was prepared following steps 5-7 in Example 1 using tert-butyl N-(2-carbamoylallyl)carbamate for the olefin.

$^1$H NMR (400 MHz, D2O) δ 4.18 (d, J=6.4 Hz, 1H), 4.10 (s, 1H), 3.57-3.51 (m, 1H), 3.45-3.41 (m, 1.6H), 3.32-3.25 (m, 2.4H), 3.13 (t, J=12.4 Hz, 1H), 2.94 (d, J=12.4 Hz, 0.6H), 2.83 (d, J=11.6 Hz, 0.4H), 2.06-1.77 (m, 4H)

Examples 15 and 16

[(2S)-2-[(5R)-5-(aminomethyl)-4,5-dihydroisoxazol-3-yl]-7-oxo-1,6-diazabicyclo[3.2.1]octan-6-yl]hydrogen sulfate

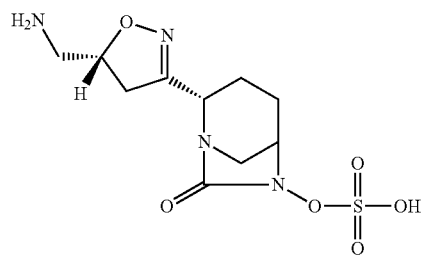 [SMILES: NC[C@H]1CC([C@@H]2CCC3CN2C(=O)N3OS(=O)(=O)O)=NO1]

[(2S)-2-[(5S)-5-(aminomethyl)-4,5-dihydroisoxazol-3-yl]-7-oxo-1,6-diazabicyclo[3.2.1]octan-6-yl]hydrogen sulfate

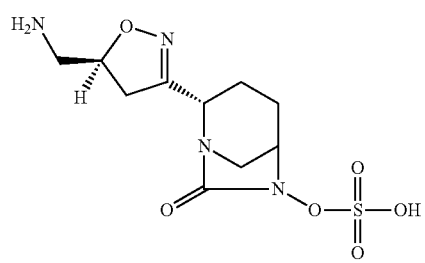 [SMILES: NC[C@@H]1CC([C@@H]2CCC3CN2C(=O)N3OS(=O)(=O)O)=NO1]

Step 1: Separation of stereoisomers of intermediate for example 2 with chiral column tert-butyl N-[[(5R)-3-[(2S,5R)-6-benzyloxy-7-oxo-1,6-diazabicyclo[3.2.1]octan-2-yl]-4,5-dihydroisoxazol-5-yl]methyl]carbamate

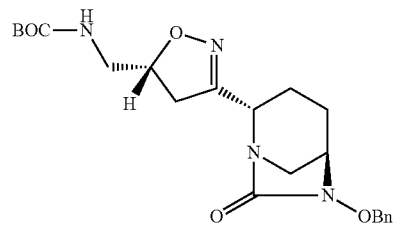 [SMILES: CC(C)(C)OC(=O)NC[C@H]1CC([C@@H]2CC[C@@H]3CN2C(=O)N3OCc2ccccc2)=NO1]

tert-butyl N-[[(5S)-3-[(2S,5R)-6-benzyloxy-7-oxo-1,6-diazabicyclo[3.2.1]octan-2-yl]-4,5-dihydroisoxazol-5-yl]methyl]carbamate

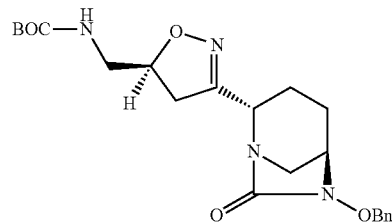 [SMILES: CC(C)(C)OC(=O)NC[C@@H]1CC([C@@H]2CC[C@@H]3CN2C(=O)N3OCc2ccccc2)=NO1]

Chromatographic Conditions
column: Chiralpak® IB, 5 um, 20×250 mm
Column Temperature: 25° C.
Mobile Phase: 2-Propanol (10%)/n-Hexane (90%)
Flow Rate: 20 mL/min
Detection: 254 nm
Injection Volume: 2 mL
Sample preparation: Intermediate-A (100 mg) was dissolved in methylene dichloride (2 mL)
Retention Time: Less polar isomer 22 minutes, More polar isomer 27 minutes
Less polar isomer—$^1$H NMR (400 MHz CDCl$_3$) δ 7.44-7.35 (m, 5H), 5.08 (d, J=11.2 Hz, 1H), 4.09 (d, J=11.2 Hz, 1H), 4.82 (s, 1H), 4.74 (m, 1H), 4.13 (d, J=6.8 Hz, 1H), 3.37-3.26 (m, 3H), 3.05-2.70 (m, 4H), 2.20-1.75 (m, 4H), 1.42 (s, 9H).
More polar isomer—$^1$H NMR (400 MHz CDCl$_3$) δ 7.52-7.35 (m, 5H), 5.07 (d, J=11.6 Hz, 1H), 4.89 (d, J=11.6 Hz, 1H), 4.72 (m, 1H), 4.14 (d, J=7.2 Hz, 1H), 3.37-3.08 (m, 4H), 2.92-2.68 (m, 3H), 2.20-1.72 (m, 4H), 1.44 (s, 9H).

Step 2: Isolated Chiral Isomers were Treated According to Same Procedure as Step 6 and 7 in Example 1 to Give Example 15 (from LP) and 16 (from MP)

From LP isomer (Example 15)—$^1$H NMR (400 MHz, D$_2$O) δ 5.04 (m, 1H), 4.30 (d, J=6.8 Hz, 1H), 4.23 (s, 1H), 3.42-2.96 (m, 6H), 2.19-1.87 (m, 4H).
From MP isomer (Example 16)—$^1$H NMR (400 MHz, D$_2$O) δ 5.04 (m, 1H), 4.30 (d, J=6.4 Hz, 1H), 4.22 (s, 1H), 3.47-2.90 (m, 6H), 2.05-1.87 (m, 4H).

Example 17 and 18

[(2S,5R)-2-[(5R)-1-oxa-2,7-diazaspiro[4.4]non-2-en-3-yl]-7-oxo-1,6-diazabicyclo[3.2.1]octan-6-yl]hydrogen sulfate

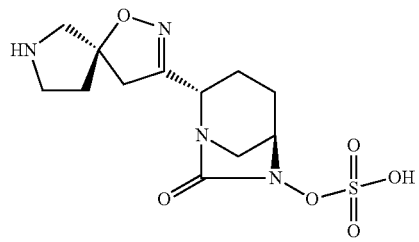 [SMILES: O=C1N2C[C@@H](CC[C@H]2C2=NO[C@]3(CCNC3)C2)N1OS(=O)(=O)O]

[(2S,5R)-2-[(5S)-1-oxa-2,7-diazaspiro[4.4]non-2-en-3-yl]-7-oxo-1,6-diazabicyclo[3.2.1]octan-6-yl]hydrogen sulfate

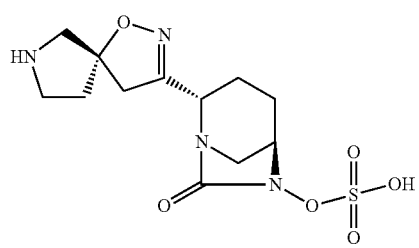 [SMILES: O=C1N2C[C@@H](CC[C@H]2C2=NO[C@@]3(CCNC3)C2)N1OS(=O)(=O)O]

Step 1: Separation of stereoisomers of intermediate for example 9 with chiral column tert-butyl (5R)-3-[(2S,5R)-6-benzyloxy-7-oxo-1,6-diazabicyclo[3.2.1]octan-2-yl]-1-oxa-2,7-diazaspiro[4.4]non-2-ene-7-carboxylate

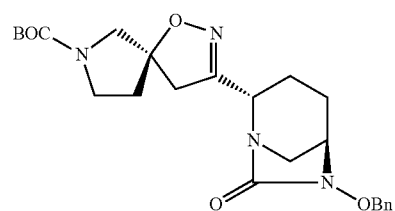 [SMILES: CC(C)(C)OC(=O)N1CC[C@@]2(CC([C@@H]3CC[C@@H]4CN3C(=O)N4OCc3ccccc3)=NO2)C1]

tert-butyl (5S)-3-[(2S,5R)-6-benzyloxy-7-oxo-1,6-diazabicyclo[3.2.1]octan-2-yl]-1-oxa-2,7-diazaspiro[4.4]non-2-ene-7-carboxylate

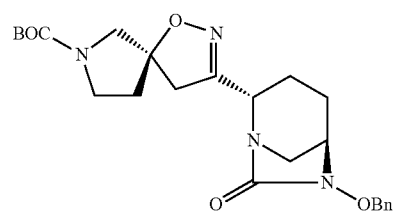 [SMILES: CC(C)(C)OC(=O)N1CC[C@@]2(CC([C@@H]3CC[C@@H]4CN3C(=O)N4OCc3ccccc3)=NO2)C1]

Column: Chiralpak® IB, 5 um, 20×250 mm
Column Temperature: 25° C.
Mobile Phase: Ethanol (20%)/n-Hexane (80%)
Flow Rate: 20 mL/min
Detection: 254 nm
Injection Volume: 2 mL
Sample preparation: Intermediate-A (50 mg) was dissolved in methylene dichloride (2 mL)
Retention Time: less polar isomer at 10 minutes, more polar isomer at 13 minutes
Less Polar isomer—$^1$H NMR (400 MHz CDCl$_3$) δ 7.42-7.37 (m, 5H), 5.07 (d, J=11.2 Hz, 1H), 4.91 (d, J=11.2 Hz, 1H), 4.16 (s, 1H), 3.71-3.33 (m, 5H), 3.11-2.71 (m, 4H), 2.21-1.76 (m, 6H), 1.46 (s, 9H).
More Polar isomer—$^1$H NMR (400 MHz CDCl$_3$) δ 7.42-7.37 (m, 5H), 5.06 (d, J=11.2 Hz, 1H), 4.91 (d, J=11.2 Hz, 1H), 3.68-3.33 (m, 5H), 3.07-2.74 (m, 4H), 2.20-1.78 (m, 6H), 1.46 (s, 9H).

Step 2: Isolated Chiral Isomers were Treated According to the Same Procedure as Step 6 and 7 in Example 1 to Give Example 17 (from LP) and 18 (from MP)

From LP isomer (Example 17)—$^1$H NMR (400 MHz, D$_2$O) δ 4.26 (d, J=7.2 Hz, 1H), 4.16 (s, 1H), 3.64-2.96 (m, 8H), 2.41-1.77 (m, 6H).
From MP isomer (Example 18)—$^1$H NMR (400 MHz, D$_2$O) δ 4.32 (d, J=6.4 Hz, 1H), 4.24 (s, 1H), 3.69-3.04 (m, 8H), 2.47-1.89 (m, 6H).

Example 19: Chiral Synthesis of Example 15

[(2S)-2-[(5R)-5-(aminomethyl)-4,5-dihydroisoxazol-3-yl]-7-oxo-1,6-diazabicyclo[3.2.1]octan-6-yl]hydrogen sulfate

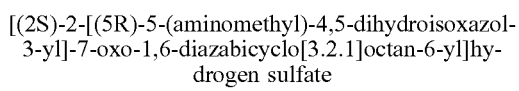

The synthesis of [(2S)-2-[(5R)-5-(aminomethyl)-4,5-dihydroisoxazol-3-yl]-7-oxo-1,6-diazabicyclo[3.2.1]octan-6-yl]hydrogen sulfate is carried out according to Scheme 4 and as outlined in the steps below. Chiral center at 5 was assigned as (R) by the known publications; 1) Tetrahedron Letters, 29, (1988), 3555-3558, 2) European Journal of Medicinal Chemistry 42 (2007) 1044-1048.

Scheme 4

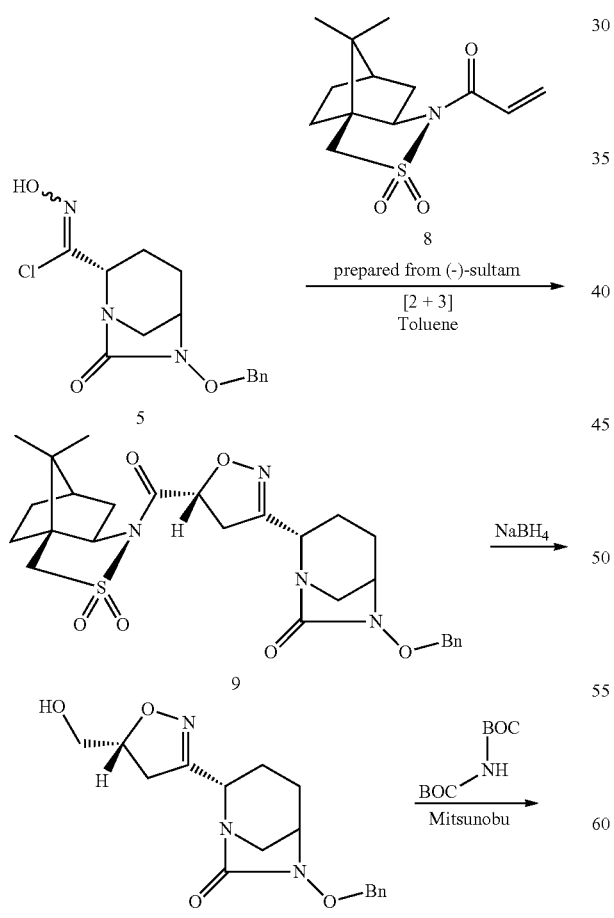

95:5 -> 99.4:0.6 (HPLC)
(Recrystallization w/EA)

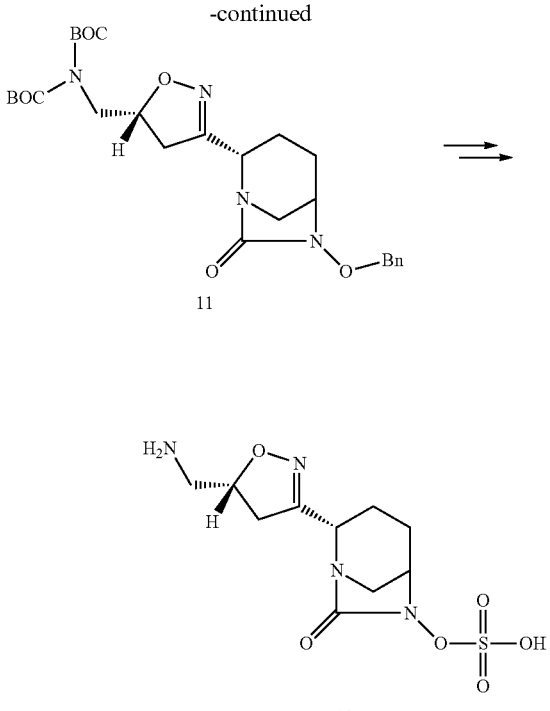

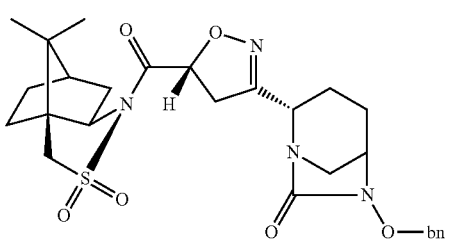

12

Step 1: (2S)-6-(benzyloxy)-2-((R)-5-((3 aS,6R, 7aR)-8,8-dimethyl-2,2-dioxidohexahydro-3H-3a,6-methanobenzo[c]isothiazole-1-carbonyl)-4,5-dihydroisoxazol-3-yl)-1,6-diazabicyclo[3.2.1]octan-7-one

9

To a solution of Compound-5 (3.3 g, 10.6 mmol) and compound-8, (R)-2-propenoyl-2,10-camphorsultam (4.28 g, 15.9 mmol, prepared from (1S)-(−)-2,10-camphorsultam and 2-propenoyl chloride) in methylene chloride (10 mL) was added TEA (2.2 mL, 15.9 mmol) dropwise at room temperature. The mixture was stirred overnight at room temperature. The mixture was washed with saturated NaHCO₃ (100 mL) and dried over anhydrous sodium sulfate. The combined organic layer was concentrated under reduced pressure and purified by silica gel column chromatography (30% EA/Hexane) to give Compound-9 (2.7 g, 47%). $^1$H NMR (400 MHz, CDCl₃) δ 7.44-7.36 (m, 5H), 5.62 (m, 1H), 5.06 (d, J=11.2 Hz, 1H), 4.90 (d, J=11.2 Hz, 1H), 4.14 (d, J=6.8 Hz, 1H), 3.89 (m, 1H), 3.56-3.20 (m, 5H), 2.88 (m, 2H), 2.22-1.77 (m, 10H), 1.44-1.25 (m, 4H), 1.87 (s, 3H), 0.98 (s, 3H).

Step 2: (2S)-6-benzyloxy-2-[(5R)-5-(hydroxymethyl)-4,5-dihydroisoxazol-3-yl]-1,6-diazabicyclo[3.2.1]octan-7-one

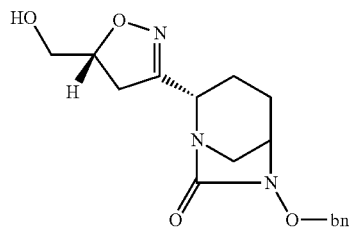

To a solution of NaBH$_4$ (140 mg, 3.69 mmol) and water (2 mL) in THF (6 mL) was added Compound-9 (1 g, 1.84 mmol) in THF (3 mL) dropwise at 0° C. The mixture was stirred for 1 h at 0° C. The reaction mixture was carefully quenched by addition of saturated NaH$_2$PO$_4$ solution (30 mL) at 0° C. The reaction mixture was diluted with water and extracted with EA (50 mL×2). The combined organic layer was concentrated and purified by silica gel column chromatography (50-100% EtOAc/n-Hexane) to give Compound-10 (500 mg, 82%). After recrystallization with EtOAc, $^1$H NMR (400 MHz, CDCl$_3$) δ 7.42-7.36 (m, 5H), 5.07 (d, J=11.2 Hz, 1H), 4.91 (d, J=11.2 Hz, 1H), 4.78 (m, 1H), 4.14 (d, J=9.0 Hz, 1H), 3.85 (m, 1H), 3.55 (m, 1H), 3.29 (s, 1H), 3.20 (m, 2H), 2.90 (d, J=12 Hz, 1H), 2.78 (d, J=19.2 Hz, 1H), 2.21-1.73 (m, 4H).

Step 3: tert-butyl N-[[(5R)-3-[(2S)-6-benzyloxy-7-oxo-1,6-diazabicyclo[3.2.1]octan-2-yl]-4, 5-dihydroisoxazol-5-yl]methyl]-N-tert-butoxycarbonyl-carbamate

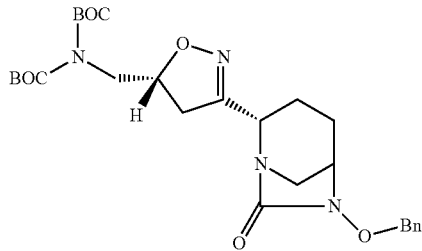

To a solution of Compound-10 (300 mg, 0.9 mmol), Di-tert-butyl-iminodicarboxylate (0.4 g, 1.8 mmol) and triphenylphosphine (0.47 g, 1.8 mmol) in THF (5 mL) was added Diisopropyl diazocarboxylate (0.36 mL, 1.84 mmol) at 0° C. The mixture was stirred overnight at room temperature. The reaction mixture was concentrated and purified by silica gel column chromatography (20-50% EtOAc/n-Hexane) to give Compound-11 (280 mg, 59%). $^1$H NMR (400 MHz, CDCl$_3$) δ 7.43-7.37 (m, 5H), 5.05 (m, 1H), 4.93-4.86 (m, 2H), 4.14 (dd, J=16.0, 6.8 Hz, 1H), 3.81-3.66 (m, 2H), 3.32 (s, 1H), 3.07-2.72 (m, 4H), 2.22-1.76 (m, 4H), 1.58 (s, 18H).

Step 4: Compound-11 was Treated According to the Same Procedure as Step 6 and 7 in Example 1 to give Example 15

B. Biological Assays

The following assay methods were used to evaluate antibacterial activity of compounds of Formula I.

Example 20: In Vitro Antibacterial Activity Assay

The in vitro antibacterial activity was evaluated by measuring MIC$_{90}$ (μg/mL) of each of the compounds of Examples 1 to 10. MIC$_{90}$ (μg/mL) is the lowest concentration of an antibiotic that will inhibit the visible growth of 90% of microorganisms after incubation as compared with a control group to which the antibiotic is not treated.

MIC values were measured by the broth microdilution method developed by the Clinical and Laboratory Standards Institute (CLSI) (see CLSI M07-A9, Methods for Dilution Antimicrobial Susceptibility Test for Bacteria that Grow Aerobically; Approved Standard-Ninth Edition (2012): CLSI, Villanova, Pa.). The in vitro antibacterial activity was measured with respect to the following 9 clinical isolates: *P. aeruginosa* (3 strains); *K. pneumoniae* (6 strains). The in vitro antibacterial activity of selected compounds was measured with respect to the following 15 clinical isolates: *K. pneumoniae* (15 strains).

Briefly, compounds (Ceftazidime, Meropenem, and LCB10-0200) were dissolved in DMSO at the concentration of 5,120 μg/mL, were diluted by two fold with DMSO, and then were diluted by twenty fold with sterilized distilled water. The final concentration in the antibacterial activity test was in the range of 0.03125 μg/mL to 64 μg/mL, and the final concentration of DMSO used as an adjuvant was 2.5% (v/v). For Ceftazidime, Meropenem, or LCB10-0200 combination studies, doubling dilutions of each compound were utilized in combination with a fixed 4 μg/mL concentration of each compounds of Examples 1 to 18.

The results of the assay for 9 clinical isolates: *P. aeruginosa* (3 strains); *K. pneumoniae* (6 strains) are summarized in Tables 2 and 3 for Ceftazidime, Tables 4, 5 and 6 for LCB10-0200 (LegoChem Biosciences, US 2012 0264727), and Table 7 for Meropenem. The results for 15 clinical isolates: *K. pneumoniae* (15 strains) are summarized in Table 8 and 9 for Meropenem, Table 10 and 11 for LCB10-0200, and Table 12 for Meropenem and LCB10-0200 with a Cubist β-lactamase inhibitor containing an isoxazole ring (Cubist-1, WO 2013/149136).

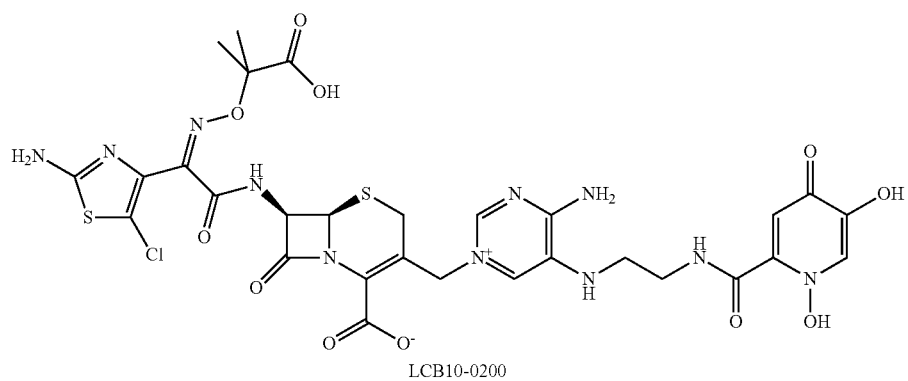

LCB10-0200

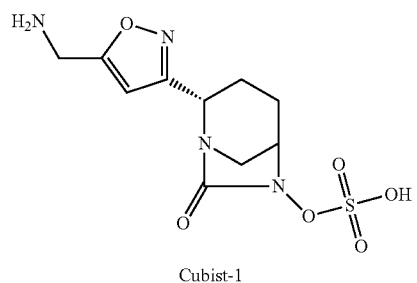

Cubist-1

In Table 12, the compound of Example 15 showed much broader coverage on various β-lactamases than Cubist-1 in combination with Meropenem and LCB10-0200.

TABLE 2

Standard BLI potentiation MIC assay in combination with Ceftazidime against a panel of clinical strains expressing β-lactamases.

| strain incubation for 19 h with BLI (4 ug/ml) | | β-lactamase content | compound Ceftazidime | | | | | | |
|---|---|---|---|---|---|---|---|---|---|
| | | | alone | OP-595 | ex 1 | ex 2 | ex 3 | ex 4 | ex 5 |
| P. aeruginosa | ATCC27853 | PoxB, AmpC | 2 | 2 | 2 | 2 | 2 | 2 | 2 |
| | ARC3506 | VEB-1, OXA-10, OprD−, AmpC | >64 | 32 | 16 | 32 | 32 | >64 | 64 |
| | ARC3514 | KPC-2, OprD−, AmpC | >64 | 8 | 8 | 16 | ND | ND | 32 |
| K. pneumoniae | ATCC700603 | SHV-3 | 32 | 0.125 | 1 | 0.5 | 1 | 2 | 0.25 |
| | NDM-506 | | >64 | 0.125 | 4 | 1 | 8 | 4 | 0.5 |
| | 5576 | SHV-11, CMY-2 DHA-1, TEM-1 | >64 | 0.125 | 16 | 1 | 4 | 8 | 0.5 |
| | 3784 | SHV-11, SHV-12, DHA-1 | >64 | 0.5 | 4 | 2 | ND | ND | 1 |
| | 4006 | SHV-12, CTX-M-15, TEM-1, OXA-9 | >64 | 0.125 | 4 | 0.5 | ND | ND | 0.125 |
| | 4248 | SHV-11, CTX-M-15, TEM-1, OXA-1 | 64 | 0.0625 | 1 | 0.125 | ND | ND | 0.0625 |

TABLE 3

Standard BLI potentiation MIC assay in combination with Ceftazidime against a panel of clinical strains expressing β-lactamases.

| strain incubation for 19 h with BLI (4 ug/ml) | | β-lactamase content | compound Ceftazidime | | | | | | |
|---|---|---|---|---|---|---|---|---|---|
| | | | alone | OP-595 | ex 6 | ex7 | ex 8 | ex 9 | ex 10 |
| P. aeruginosa | ATCC27853 | PoxB, AmpC | 2 | 2 | 2 | 2 | 2 | 2 | 2 |
| | ARC3506 | VEB-1, OXA-10, OprD−, AmpC | >64 | 32 | >64 | 32 | 64 | 32 | 32 |
| | ARC3514 | KPC-2, OprD−, AmpC | >64 | 8 | 64 | 8 | 16 | 16 | 16 |
| K. pneumoniae | ATCC700603 | SHV-3 | 32 | 0.125 | 1 | 0.125 | 2 | 0.125 | 0.25 |
| | NDM-506 | | >64 | 0.125 | 8 | 0.25 | 8 | 0.25 | 0.5 |
| | 5576 | SHV-11, CMY-2, DHA-1, TEM-1 | >64 | 0.125 | 32 | 0.25 | 16 | 0.25 | 0.25 |
| | 3784 | SHV-11, SHV-12, DHA-1 | >64 | 0.5 | 4 | 1 | 4 | 0.5 | 1 |
| | 4006 | SHV-12, CTX-M-15, TEM-1, OXA-9 | >64 | 0.125 | 4 | 0.25 | 4 | 0.0625 | 0.25 |
| | 4248 | SHV-11, CTX-M-15, TEM-1, OXA-1 | 64 | 0.0625 | 1 | 0.0625 | 1 | 0.03125 | 0.0625 |

TABLE 4

Standard BLI potentiation MIC assay in combination with LCB10-0200 against a panel of clinical strains expressing β-lactamases.

| strain incubation for 19 h with BLI (4 ug/ml) | | β-lactamase content | compound LCB10-0200 | | | | | | |
|---|---|---|---|---|---|---|---|---|---|
| | | | alone | OP-595 | ex 1 | ex 2 | ex 3 | ex 4 | ex 5 |
| P. aeruginosa | ATCC27853 | PoxB, AmpC | 0.25 | 0.25 | 0.125 | 0.25 | 0.125 | 0.125 | 0.25 |
| | ARC3506 | VEB-1, OXA-10, OprD−, AmpC | 2 | 0.25 | 0.5 | 1 | 2 | 8 | 0.25 |
| | ARC3514 | KPC-2, OprD−, AmpC | 0.25 | 0.125 | 0.125 | 0.25 | 0.0625 | 0.0625 | 0.125 |
| K. pneumoniae | ATCC700603 | SHV-3 | 1 | 0.125 | 0.125 | 0.125 | 0.125 | 0.25 | 0.125 |
| | NDM-506 | | >64 | 0.125 | 4 | 0.25 | 4 | 4 | 0.5 |
| | 5576 | SHV-11, CMY-2, DHA-1, TEM-1 | >64 | <0.03125 | 0.25 | 0.0625 | <0.03125 | 0.0625 | <0.03125 |
| | 3784 | SHV-11, SHV-12, DHA-1 | 32 | 0.0625 | 8 | 0.0625 | 16 | 16 | 0.125 |
| | 4006 | SHV-12, CTX-M-15, TEM-1, OXA-9 | 32 | <0.03125 | 0.0625 | <0.03125 | 0.0625 | 0.0625 | <0.03125 |
| | 4248 | SHV-11, CTX-M-15, TEM-1, OXA-1 | 2 | <0.03125 | <0.03125 | <0.03125 | <0.03125 | <0.03125 | <0.03125 |

TABLE 5

Standard BLI potentiation MIC assay in combination with LCB10-0200 against a panel of clinical strains expressing β-lactamases.

| strain incubation for 19 h with BLI (4 ug/ml) | | β-lactamase content | compound LCB10-0200 | | | | | | |
|---|---|---|---|---|---|---|---|---|---|
| | | | Alone | OP-595 | From ex 6 | ex7 | ex 8 | ex 9 | ex 10 |
| P. aeruginosa | ATCC27853 | PoxB, AmpC | 0.25 | 0.25 | 0.25 | 0.25 | 0.25 | 0.25 | 0.25 |
| | ARC3506 | VEB-1, OXA-10, OprD−, AmpC | 2 | 0.25 | 0.5 | 2 | 2 | 0.25 | 0.5 |
| | ARC3514 | KPC-2, OprD−, AmpC | 0.25 | 0.125 | 0.25 | 0.25 | 0.25 | 0.25 | 0.25 |
| K. pneumoniae | ATCC700603 | SHV-3 | 1 | 0.125 | 0.25 | 0.125 | 0.25 | 0.125 | 0.125 |
| | NDM-506 | | >64 | 0.125 | 16 | 0.125 | 8 | 0.125 | 0.5 |
| | 5576 | SHV-11, CMY-2, DHA-1, TEM-1 | >64 | <0.03125 | 0.5 | <0.03125 | 0.25 | <0.03125 | <0.03125 |
| | 3784 | SHV-11, SHV-12, DHA-1 | 32 | 0.0625 | 4 | 0.0625 | 16 | 0.0625 | 0.25 |
| | 4006 | SHV-12, CTX-M-15, TEM-1, OXA-9 | 32 | <0.03125 | 0.125 | <0.03125 | 0.125 | <0.03125 | <0.03125 |

TABLE 5-continued

Standard BLI potentiation MIC assay in combination with LCB10-0200 against a panel of clinical strains expressing β-lactamases.

| strain | | compound LCB10-0200 | | | | | | |
|---|---|---|---|---|---|---|---|---|
| incubation for 19 h with BLI (4 ug/ml) | β-lactamase content | Alone | OP-595 | From ex 6 | ex7 | ex 8 | ex 9 | ex 10 |
| 4248 | SHV-11, CTX-M-15, TEM-1, OXA-1 | 2 | <0.03125 | 0.0625 | <0.03125 | 0.125 | <0.03125 | <0.03125 |

TABLE 6

Standard BLI potentiation MIC assay in combination with LCB10-0200 against a panel of clinical strains expressing β-lactamases

| strain incubation for 19 h with BLI (4 ug/ml) | | β-lactamase content | compound LCB10-0200 | | | | | |
|---|---|---|---|---|---|---|---|---|
| | | | alone | OP-595 | ex 11 | ex 12 | ex 13 | ex 14 |
| P. aeruginosa | ATCC27853 | PoxB, AmpC | 0.5 | 0.5 | 0.25 | 1 | 0.5 | 0.5 |
| | ARC3506 | VEB-1, OXA-10, OprD−, AmpC | 2 | 0.25 | 0.5 | 2 | 1 | 4 |
| | ARC3514 | KPC-2, OprD−, AmpC | 0.5 | 0.25 | 0.125 | 0.5 | 0.25 | 0.25 |
| K. pneumoniae | ATCC700603 | SHV-3 | 2 | 0.125 | 0.25 | 1 | 0.25 | 0.25 |
| | NDM-506 | | >64 | >64 | 4 | >64 | >64 | >64 |
| | 5576 | SHV-11, CMY-2, DHA-1, TEM-1 | >64 | 0.0625 | 1 | 16 | 0.0625 | 1 |
| | 3784 | SHV-11, SHV-12, DHA-1 | 64 | 0.0625 | 0.25 | 64 | 0.125 | 0.25 |
| | 4006 | SHV-12, CTX-M-15, TEM-1, OXA-9 | 8 | <0.03125 | 1 | 1 | 0.0625 | 0.25 |
| | 4248 | SHV-11, CTX-M-15, TEM-1, OXA-1 | 4 | <0.03125 | <0.0312 | 0.25 | <0.03125 | <0.03125 |

TABLE 7

Standard BLI potentiation MIC assay in combination with Meropenem against a panel of clinical strains expressing β-lactamases

| strain incubation for 19 h with BLI (4 ug/ml) | | β-lactamase content | compound Meropenem | | | | |
|---|---|---|---|---|---|---|---|
| | | | alone | OP-595 | ex 12 | ex 13 | ex 14 |
| P. aeruginosa | ATCC27853 | PoxB, AmpC | 2 | 2 | 2 | 2 | 2 |
| | ARC3506 | VEB-1, OXA-10, OprD−, AmpC | 64 | 64 | 64 | 32 | 64 |
| | ARC3514 | KPC-2, OprD−, AmpC | >64 | >64 | >64 | >64 | >64 |
| K. pneumoniae | ATCC700603 | SHV-3 | 0.125 | 0.125 | 0.25 | 0.125 | 0.125 |
| | NDM-506 | | >64 | >64 | >64 | >64 | >64 |
| | 5576 | SHV-11, CMY-2, DHA-1, TEM-1 | 1 | 0.03125 | 0.25 | 0.0625 | 0.0625 |
| | 3784 | SHV-11, SHV-12, DHA-1 | 2 | 0.25 | 1 | 0.25 | 0.25 |
| | 4006 | SHV-12, CTX-M-15, TEM-1, OXA-9 | 0.5 | 0.0625 | 1 | 0.0625 | 0.0625 |
| | 4248 | SHV-11, CTX-M-15, TEM-1, OXA-1 | 0.125 | 0.0625 | 0.125 | 0.0625 | 0.0625 |

TABLE 8

Standard BLI potentiation MIC assay in combination with Meropenem against a panel of K. pneumoniae clinical strains expressing β-lactamases.

| strain incubation for 19 h with BLI (4 ug/ml) | | β-lactamase content | compound Meropenem | | | | |
|---|---|---|---|---|---|---|---|
| | | | alone | OP-595 | ex 12 | ex 13 | ex 14 |
| K. pneumoniae | ATCC700603 | | 0.25 | 0.125 | 0.25 | 0.125 | 0.025 |
| | 4006 | SHV-12, CTX-M-15, TEM-1, OXA-9 | 1 | 0.0625 | 0.5 | 0.125 | 0.25 |
| | 5216 | TEM-1A | 64 | 2 | 64 | 32 | 32 |
| | 7586 | | 64 | 8 | 64 | 32 | 16 |
| | 6540 | | 1 | 0.125 | 1 | 0.25 | 0.125 |
| | 6839 | SHV-11, SHV-12, DHA-1 | 4 | 0.25 | 4 | 0.5 | 0.5 |
| | 89 | | 8 | 4 | 4 | 4 | 4 |
| | 100 | | 4 | 4 | 8 | 4 | 4 |
| | 101 | | >64 | 0.125 | 8 | 0.125 | 0.125 |
| | 23 | | 16 | 16 | 16 | 16 | 16 |
| | 5971(KOX) | | 64 | 16 | 64 | 16 | 16 |
| | KU2 | | >64 | >64 | >64 | >64 | >64 |
| | MP14 | | >64 | 0.5 | >64 | 1 | 1 |
| | 5117 | SHV-11, TEM-1 | 8 | 0.5 | 8 | 2 | 2 |
| | 5576 | SHV-11, CMY-2, DHA-1, TEM-1 | 1 | 0.0625 | 2 | 0.0625 | 0.25 |

TABLE 9

Standard BLI potentiation MIC assay in combination with Meropenem against a panel of K. pneumoniae clinical strains expressing β-lactamases.

| strain incubation for 19 h with BLI (4 ug/ml) | | β-lactamase content | compound Meropenem | | | | | | | |
|---|---|---|---|---|---|---|---|---|---|---|
| | | | alone | Avibactam | OP-595 | ex 15 | ex 16 | ex 17 | ex 18 | ex 5 |
| K. pneumoniae | ATCC700603 | | 0.125 | 0.0625 | 0.0625 | 0.0625 | 0.0625 | 0.0625 | 0.0625 | <0.0312 |
| | 4006 | SHV-12, CTX-M-15, TEM-1, OXA-9 | 0.5 | 0.125 | 0.0625 | 0.0625 | 0.125 | 0.0625 | 0.125 | <0.0312 |
| | 5216 | TEM-1A | 32 | 8 | 2 | 2 | 8 | 2 | 8 | 8 |
| | 7586 | | 16 | 8 | 2 | 2 | 4 | 2 | 4 | 4 |
| | 6540 | | 0.5 | 0.0625 | 0.0625 | 0.0625 | 0.0625 | 0.0625 | 0.0625 | <0.0312 |
| | 6839 | SHV-11, SHV-12, DHA-1 | 2 | 0.5 | 0.0625 | 0.0625 | 0.0625 | 0.0625 | 0.0625 | 0.25 |
| | 89 | | 4 | 2 | 2 | 1 | 2 | 1 | 1 | 2 |
| | 100 | | 4 | 4 | 2 | 2 | 2 | 2 | 2 | 2 |
| | 101 | | 64 | 0.125 | 0.0625 | 0.0625 | 0.0625 | 0.0625 | 0.0625 | <0.0312 |
| | 23 | | 1 | 1 | 2 | 1 | 1 | 1 | 1 | 4 |
| | 5971(KOX) | | 64 | 64 | 4 | 4 | 16 | 4 | 4 | 4 |
| | KU2 | | >64 | 32 | 8 | 32 | 32 | 8 | 16 | >64 |
| | MP14 | | 64 | 0.125 | 0.125 | 0.125 | 0.125 | 0.125 | 0.125 | 0.125 |
| | 5117 | SHV-11, TEM-1 | 4 | 1 | 0.25 | 0.25 | 1 | 0.25 | 1 | 0.5 |
| | 5576 | SHV-11, CMY-2, DHA-1, TEM-1 | 1 | 0.0625 | <0.0312 | <0.0312 | 0.0625 | <0.0312 | <0.0312 | <0.0312 |

TABLE 10

Standard BLI potentiation MIC assay in combination with LCB10-0200 against a panel of *K. pneumoniae* clinical strains expressing β-lactamases.

| strain incubation for 19 h with BLI (4 ug/ml) | | β-lactamase content | compound LCB10-0200 | | | | |
|---|---|---|---|---|---|---|---|
| | | | alone | OP-595 | ex 12 | ex 13 | ex 14 |
| *K. pneumoniae* | ATCC700603 | | 0.5 | 0.125 | 0.5 | 0.25 | 0.125 |
| | 4006 | SHV-12, CTX-M-15, TEM-1, OXA-9 | 4 | 0.03125 | 4 | 0.125 | 0.125 |
| | 5216 | TEM-1A | >64 | 0.25 | >64 | 64 | >64 |
| | 7586 | | 4 | 0.03125 | 2 | 0.5 | 0.25 |
| | 6540 | | 0.5 | <0.03125 | 0.25 | 0.0625 | 0.03125 |
| | 6839 | SHV-11, SHV-12, DHA-1 | 32 | <0.03125 | 64 | 0.125 | 0.125 |
| | 89 | | 0.125 | 0.0625 | 0.0625 | 0.0625 | 0.0625 |
| | 100 | | 0.0625 | 0.0625 | 0.0625 | 0.0625 | 0.125 |
| | 101 | | 16 | <0.03125 | 8 | 0.0625 | <0.03125 |
| | 23 | | 1 | 1 | 1 | 1 | 1 |
| | 5971(KOX) | | 32 | 8 | 64 | 64 | 16 |
| | KU2 | | 32 | 8 | 32 | 32 | 32 |
| | MP14 | | 0.125 | 0.03125 | 0.25 | 0.125 | 0.0625 |
| | 5117 | SHV-11, TEM-1 | 0.125 | 0.0625 | 0.25 | 0.0625 | 0.0625 |
| | 5576 | SHV-11, CMY-2, DHA-1, TEM-1 | >64 | <0.03125 | 16 | 0.125 | 1 |

TABLE 11

Standard BLI potentiation MIC assay in combination with LCB10-0200 against a panel of *K. pneumoniae* clinical strains expressing β-lactamases.

| strain incubation for 19 h with BLI (4 ug/ml) | | β-lactamase content | compound LCB10-0200 | | | | | | | |
|---|---|---|---|---|---|---|---|---|---|---|
| | | | alone | Avibactam | OP-595 | ex 15 | ex 16 | ex 17 | ex 18 | ex 5 |
| *K. pneumoniae* | ATCC700603 | | 0.5 | 0.25 | 0.125 | 0.125 | 0.25 | 0.125 | 0.125 | 0.125 |
| | 4006 | SHV-12, CTX-M-15, TEM-1, OXA-9 | 4 | <0.0312 | <0.0312 | <0.0312 | 0.25 | <0.0312 | 0.0312 | 0.0312 |
| | 5216 | TEM-1A | 64 | 4 | 0.5 | 0.5 | 16 | 0.25 | 2 | 2 |
| | 7586 | | 4 | 0.125 | 0.0625 | 0.0625 | 0.5 | <0.0312 | 0.25 | 0.25 |
| | 6540 | | 4 | 0.125 | 0.0625 | 0.0625 | 0.125 | <0.0312 | <0.0312 | <0.0312 |
| | 6839 | SHV-11, SHV-12, DHA-1 | 16 | 8 | <0.0312 | <0.0312 | 8 | <0.0312 | 0.0625 | 0.0625 |
| | 89 | | 0.125 | 0.0625 | 0.0625 | 0.0625 | 0.125 | <0.0312 | 0.0312 | 0.0312 |
| | 100 | | 0.0625 | 0.0625 | 0.0625 | 0.0625 | 0.125 | 0.0625 | <0.0312 | <0.0312 |
| | 101 | | 32 | 1 | 0.25 | 0.25 | 0.25 | <0.0312 | <0.0312 | <0.0312 |
| | 23 | | 0.125 | 0.125 | <0.0312 | <0.0312 | <0.0312 | <0.0312 | 0.0312 | 0.0312 |
| | 5971(KOX) | | 64 | 64 | 16 | 16 | 64 | 8 | 16 | 16 |
| | KU2 | | 32 | 16 | 2 | 2 | 16 | 2 | 16 | 16 |
| | MP14 | | 0.125 | <0.0312 | <0.0312 | <0.0312 | 0.0625 | <0.0312 | <0.0312 | <0.0312 |
| | 5117 | SHV-11, TEM-1 | 0.125 | 0.125 | <0.0312 | <0.0312 | 0.0625 | <0.0312 | 0.0625 | 0.0625 |
| | 5576 | SHV-11, CMY-2, DHA-1, TEM-1 | 64 | 0.25 | 0.0625 | 0.0625 | 0.25 | <0.0312 | <0.0312 | <0.0312 |

TABLE 12

Standard BLI potentiation MIC assay in combination with Meropenem/
LCB10-0200 against a panel of K. pneumoniae clinical strains expressing β-lactamases.
(isoxazoline vs. isoxazole)

| strain | | β-lactamase content | compound | | | | | | | |
|---|---|---|---|---|---|---|---|---|---|---|
| incubation for 19 h | | | Meropenem | | | | LCB10-0200 | | | |
| with BLI (4 ug/ml) | | | alone | OP-595 | ex 15 | Cubist-1 | alone | OP-595 | ex 15 | Cubist-1 |
| K. pneumoniae | ATCC700603 | | 0.125 | 0.0625 | 0.0625 | 0.0625 | 0.5 | 0.125 | 0.125 | 0.25 |
| | 4006 | SHV-12, CTX-M-15, TEM-1, OXA-9 | 0.5 | <0.0312 | 0.0625 | 0.125 | 8 | <0.0312 | <0.0312 | 0.25 |
| | 5216 | TEM-1A | 32 | 2 | 2 | 8 | 32 | 0.25 | 0.5 | 1 |
| | 7586 | | 16 | 1 | 2 | 16 | 2 | <0.0312 | 0.0625 | 0.5 |
| | 6540 | | 0.5 | 0.0625 | 0.0625 | 0.0625 | 2 | <0.0312 | 0.0625 | 0.0625 |
| | 6839 | SHV-11, SHV-12, DHA-1 | 2 | 0.125 | 0.0625 | 0.25 | 32 | 0.0625 | <0.0312 | 16 |
| | 89 | | 2 | 1 | 1 | 0.125 | 0.0625 | <0.0312 | 0.0625 | <0.0312 |
| | 100 | | 4 | 1 | 2 | 0.5 | 0.0625 | 0.0625 | 0.0625 | 0.0625 |
| | 101 | | 32 | <0.0312 | 0.0625 | 0.0625 | 32 | <0.0312 | 0.25 | 4 |
| | 23 | | 2 | 2 | 1 | 2 | 0.25 | <0.0312 | <0.0312 | 0.125 |
| | 5971(KOX) | | 32 | 2 | 4 | 32 | 32 | 8 | 16 | 32 |
| | KU2 | | >64 | 8 | 32 | 16 | 32 | 2 | 2 | 16 |
| | MP14 | | 64 | 0.125 | 0.125 | 0.125 | 0.25 | <0.0312 | <0.0312 | 0.0625 |
| | 5117 | SHV-11, TEM-1 | 4 | 0.25 | 0.25 | 4 | 0.25 | <0.0312 | <0.0312 | 0.125 |
| | 5576 | SHV-11, CMY-2, DHA-1, TEM-1 | 1 | <0.0312 | <0.0312 | <0.0625 | 64 | <0.0312 | 0.0625 | 0.25 |

Example 21—Inhibitory Activity Against β-Lactamases (IC$_{50}$ Determination)

Four compounds (Avibactam, OP-595, Ex15 and Ex17) were dissolved in T.D.W at 10 mM. More diluted stocks were prepared as necessary. Enzyme activity was determined by monitoring the change of absorbance at 492 nm using the characteristic molecular extinction coefficient ($\Delta\epsilon_{492}$=17,400 M$^{-1}$ cm$^{-1}$) of nitrocefin by a Shimazu UV-1650PC spectrophotometer. The nitrocefin was purchased from OXOID. Kinetic measurements were run at 30° C. in 10 mM MES[2-(N-morpholino)ethanesulfonic acid] buffer (pH 6.8) or 10 mM MES[2-(N-morpholino)ethanesulfonic acid] buffer (pH 6.8), 20 mg/ml BSA and 50 mM sodium bicarbonate. Reactions were performed in 2.5 mL cuvettes with 100 µM nitrocefin and initiated by adding 1.5 nM to 2.5 nM enzyme. The first 180 s of each reaction was used to measure initial rates. Data were evaluated using Microsoft Excel. Concentration dependent inhibition of enzyme was measured using different concentrations of inhibitors resulting from two-fold dilution series. Reaction progress at every concentration of inhibitor was measured in triplicates. IC$_{50}$ values were calculated using 4-parameter log fits using XL Fit curve fitting software (www.idbs.com) for Excel using the following equation:

$$y = A + \frac{B - A}{1 + \left(\frac{x}{IC_{50}}\right)^{slope}}$$

where y is the remaining enzyme activity (in %) and x is the corresponding concentration. The fitted IC$_{50}$ parameter is the relative IC$_{50}$, and is defined as the concentration giving a response half way between the fitted top (B) and bottom (A) of the curve.

TABLE 13

IC$_{50}$ values (µM) of selected comounds

| β-lactamase | Molecular class | Avibactam (µM) | OP-0595 | Ex 17 | Ex 15 |
|---|---|---|---|---|---|
| KPC-3 | A | 3.4715 | 0.0637 | 2.74 | 3.03 |
| CTX-M-15 | A | NT | NT | NT | NT |
| NDM-1 | B | NI | NI | 1191 | 1652 |
| CMY-10 | C | 0.013 | 42.58 | 0.185 | 0.123 |
| OXA-48 | D | 5.10 | 44.17 | 29.54 | 6.42 |

TABLE 14

MICs of bacterial strains used for extraction of enzymes (BLI: 4 ug/mL)

| strain | | β-lactamase content | Meropenem | | | | LCB10-0200 | | | |
|---|---|---|---|---|---|---|---|---|---|---|
| with BLI (4 mg/ml) | | | Alone | Avibactam | OP-595 | Ex 17 | Alone | Avibactam | OP-595 | Ex 17 |
| K. pneumoniae | 4006 | SHV-12, CTX-M-15, TEM-1, OXA-9 | 1 | 0.5 | 0.0625 | 0.0625 | 4 | 0.25 | 0.0625 | 0.0625 |
| | 5576 | SHV-11, CMY-2, DHA-1, TEM-1 | 2 | 0.25 | 0.0625 | 0.0625 | 32 | 0.125 | <0.0312 | <0.0312 |
| | CL5761 | KPC-3, TEM-216, SHV-5 | >64 | 1 | 1 | 0.5 | 32 | 16 | 0.25 | 0.125 |

TABLE 14-continued

MICs of bacterial strains used for extraction of enzymes (BLI: 4 ug/mL)

| strain | | | Meropenem | | | | LCB10-0200 | | | |
|---|---|---|---|---|---|---|---|---|---|---|
| | with BLI (4 mg/ml) | β-lactamase content | Alone | Avibactam | OP-595 | Ex 17 | Alone | Avibactam | OP-595 | Ex 17 |
| *E. coli* | ECO200 | NDM-1, TEM-1, CTX-M-15, EC (AmpC), OXA-2 type | >64 | >64 | <0.0312 | <0.0312 | >64 | >64 | <0.0312 | <0.0312 |
| | K0519020 | CTX-M-15, TEM-1, OXA-1, AmpC (NC_000913) | 1 | 0.25 | 0.125 | 0.0625 | 64 | 0.25 | 0.0625 | <0.0312 |
| | TOPOXA048 | OXA-48, TEM-116, AmpC (NC_000913) | 0.25 | 0.5 | <0.0312 | <0.0312 | 0.25 | 0.25 | <0.0312 | <0.0312 |
| *E. aerogenes* | K9911729 | CMY-10, TEM-1, SHV-12, AmpC (DQ478697) | 0.5 | 0.5 | <0.0312 | <0.0312 | 2 | 2 | <0.0312 | <0.0312 |

Example 22—Mouse Pharmacokinetics

The pharmacokinetics values were evaluated in a mouse model. The test compound (50 mg/kg) was injected into the tail vein of 8 week old ICR mouse, weighing approximately 26-30 g. Blood samples were taken from inferior vena cava at 5 min, 15 min, 30 min, 1 h, 1.5 h, 2 h, 3 h, 4 h, and 8 h after administration, plasma was separated, and quantified by using LC-MS/MS. See FIG. 1, Panels A-C. Lab conditions were temperature of 22±3° C. and humidity of 50±20%.

The results from the compounds of Example 2, 5, and 17 are summarized in Table 15.

TABLE 15

| | Mouse (IV, 50 mg/kg) | | |
|---|---|---|---|
| Parameter | Compound of Example 2 | Compound of Example 5 | Compound of Example 17 |
| $AUC_{inf}$ (mg * h/l) | 34.54 ± 3.61 | 55.29 ± 4.16 | 30.96 ± 0.50 |
| $AUC_{norm}$ (kg * h/l) | 0.69 ± 0.07 | 1.11 ± 0.08 | 0.62 ± 0.01 |
| CL (l/h/kg) | 1.46 ± 0.16 | 0.91 ± 0.07 | 1.62 ± 0.03 |
| $V_{ss}$ (l/kg) | 1.57 ± 0.12 | 2.23 ± 0.61 | 1.81 ± 0.14 |
| $C_{max}$ (mg/l) | 74.37 ± 3.44 | 103.2 ± 9.93 | 64.17 ± 3.88 |
| $C_{max,norm}$ (kg/l) | 1.49 ± 0.07 | 2.06 ± 0.20 | 1.28 ± 0.08 |
| $T_{max}$ (h) | 0.08 ± 0.00 | 0.08 ± 0.00 | 0.08 ± 0.00 |
| $T_{1/2}$ (h) | 1.47 ± 0.16 | 3.19 ± 1.56 | 1.25 ± 0.15 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

The invention claimed is:

1. A compound having a structure of Formula I or a pharmaceutically acceptable salt thereof:

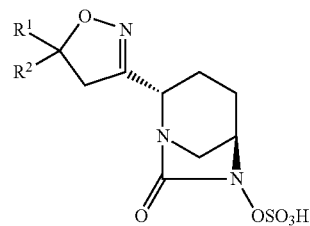

I wherein
R$^1$ and R$^2$ are each independently H, hydroxyalkyl, —C(O)—NH$_2$, amido-, amino-, or guanidino-substituted alkyl, amido-, amino-, or guanidino-substituted alkoxyalkyl, or —(CH$_2$)$_p$—O—NHR$^3$, or
R$^1$ and R$^2$ combine to form an amino- or guanidino-substituted cycloalkyl ring, or an optionally substituted nitrogen-containing heterocyclyl ring;
p is an integer from 1 to 6; and
R$^3$ is, independently for each occurrence, H, lower alkyl, or —C(=NH)NH$_2$.

2. The compound of claim 1, wherein at least one of R$^1$ and R$^2$ is independently

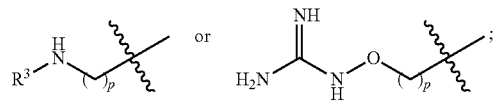

wherein p is an integer from 1 to 5.

3. The compound of claim 1, wherein R$^1$ and R$^2$ combine to form a structure of Formula A

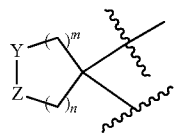

A wherein
Y and Z are each independently CHR$^4$, NR$^5$, or absent;
R$^4$ is, independently for each occurrence, H, amido-, amino-, or guanidino-substituted lower alkyl, or NHR$^3$;

R⁵ is, independently for each occurrence, H, amido-, amino-, or guanidino-substituted lower alkyl, or —C(=NH)NH₂; and m and n are each independently an integer from 1 to 3; provided that both Y and Z are not absent.

4. The compound of claim 1, wherein the compound has the structure of formula II or a pharmaceutically acceptable salt thereof:

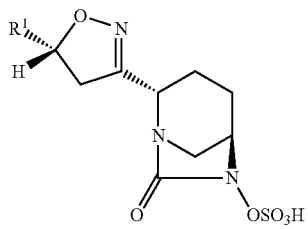

II and R¹ is an amido-, amino-, or guanidino substituted alkyl, an amido-, amino-, or guanidino-substituted alkoxyalkyl, or —(CH₂)ₚ—O—NHR³.

5. The compound of claim 1, wherein the compound has the structure of formula III or a pharmaceutically acceptable salt thereof:

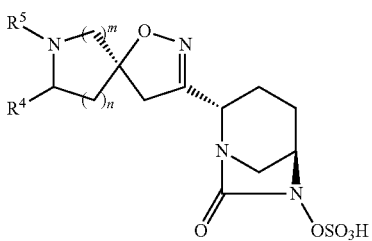

III and m is less than or equal to n.

6. The compound of claim 1, wherein the compound is:

[(2S,5R)-2-[5-(2-aminoethyl)-4,5-dihydroisoxazol-3-yl]-7-oxo-1,6-diazabicyclo[3.2.1]octan-6-yl]hydrogen sulfate,

[(2S, 5R)-2-[5-(aminomethyl)-4,5-dihydroisoxazol-3-yl]-7-oxo-1,6-diazabicyclo[3.2.1]octan-6-yl]hydrogen sulfate,

[(2S, 5R)-2-[5-(3-aminopropyl)-4,5-dihydroisoxazol-3-yl]-7-oxo-1,6-diazabicyclo[3.2.1]octan-6-yl]hydrogen sulfate,

[(2S, 5R)-2-[5-(guanidinooxymethyl)-4,5-dihydroisoxazol-3-yl]-7-oxo-1,6-diazabicyclo[3.2.1]octan-6-yl]hydrogen sulfate,

[(2S, 5R)-2-[5,5-bis(aminomethyl)-4H-isoxazol-3-yl]-7-oxo-1,6-diazabicyclo[3.2.1]octan-6-yl]hydrogen sulfate,

[(2S, 5R)-2-(1-oxa-2,7,8-triazaspiro[4.4]non-2-en-3-yl)-7-oxo-1,6-diazabicyclo[3.2.1]octan-6-yl]hydrogen sulfate,

[(2S, 5R)-2-(5-oxa-2,6-diazaspiro[3.4]oct-6-en-7-yl)-7-oxo-1,6-diazabicyclo[3.2.1]octan-6-yl]hydrogen sulfate,

[(2S, 5R)-2-(2-amino-5-oxa-6-azaspiro[3.4]oct-6-en-7-yl)-7-oxo-1,6-diazabicyclo[3.2.1]octan-6-yl]hydrogen sulfate,

[(2S, 5R)-2-(1-oxa-2,7-diazaspiro[4.4]non-2-en-3-yl)-7-oxo-1,6-diazabicyclo[3.2.1]octan-6-yl]hydrogen sulfate,

[(2S, 5R)-2-(1-oxa-2,8-diazaspiro[4.5]dec-2-en-3-yl)-7-oxo-1,6-diazabicyclo[3.2.1]octan-6-yl]hydrogen sulfate,

[(2S,5R)-2-(8-carbamimidoyl-1-oxa-2,8-diazaspiro[4.5]dec-2-en-3-yl)-7-oxo-1,6-diazabicyclo[3.2.1]octan-6-yl]hydrogen sulfate,

[(2S,5R)-2-[7-(2-amino-2-oxo-ethyl)-1-oxa-2,7-diazaspiro[4.4]non-2-en-3-yl]-7-oxo-1,6-diazabicyclo[3.2.1]octan-6-yl]hydrogen sulfate,

[(2S, 5R)-2-[5-(aminomethyl)-5-(hydroxymethyl)-4H-isoxazol-3-yl]-7-oxo-1,6-diazabicyclo[3.2.1]octan-6-yl]hydrogen sulfate,

[(2S,5R)-2-[5-(aminomethyl)-5-carbamoyl-4H-isoxazol-3-yl]-7-oxo-1,6-diazabicyclo[3.2.1]octan-6-yl]hydrogen sulfate,

[(2S)-2-[(5R)-5-(aminomethyl)-4,5-dihydroisoxazol-3-yl]-7-oxo-1,6-diazabicyclo[3.2.1]octan-6-yl]hydrogen sulfate,

[(2S)-2-[(5 S)-5-(aminomethyl)-4,5-dihydroisoxazol-3-yl]-7-oxo-1,6-diazabicyclo[3.2.1]octan-6-yl]hydrogen sulfate,

[(2S,5R)-2-[(5R)-1-oxa-2,7-diazaspiro[4.4]non-2-en-3-yl]-7-oxo-1,6-diazabicyclo[3.2.1]octan-6-yl]hydrogen sulfate,

[(2S,5R)-2-[(5 S)-1-oxa-2,7-diazaspiro[4.4]non-2-en-3-yl]-7-oxo-1,6-diazabicyclo[3.2.1]octan-6-yl]hydrogen sulfate, or a pharmaceutically acceptable salt thereof.

7. A method for inhibiting β-lactamase, the method comprising contacting the β-lactamase with a compound of claim 1.

8. The method of claim 7, wherein at least one of R¹ and R² is independently

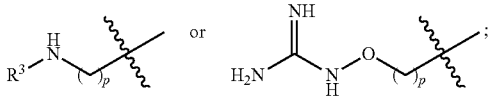

wherein p is an integer from 1 to 5.

9. The method of claim 7, wherein R¹ and R² combine to form a structure of Formula A

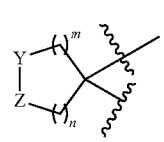

A wherein

Y and Z are each independently CHR⁴, NR⁵, or absent;

R⁴ is, independently for each occurrence, H, amido-, amino-, or guanidino-substituted lower alkyl, or NHR³;

R⁵ is, independently for each occurrence, H, amido-, amino-, or guanidino-substituted lower alkyl or —C(=NH)NH₂; and m and n are each independently an integer from 1 to 3; provided that both Y and Z are not absent.

10. A method for inhibiting β-lactamase, the method comprising contacting the β-lactamase with a compound of claim 4.

11. A method for inhibiting β-lactamase, the method comprising contacting the β-lactamase with a compound of claim 5.

12. A method for inhibiting β-lactamase, the method comprising contacting the β-lactamase with a compound of claim 6.

13. The compound of claim 1, wherein the compound is [(2S, 5R)-2-[5,5-bis(aminomethyl)-4H-isoxazol-3-yl]-7-oxo-1,6-diazabicyclo[3.2.1]octan-6-yl]hydrogen sulfate or a pharmaceutically acceptable salt thereof.

14. The compound of claim 1, wherein the compound is [(2S, 5R)-2-[5-(aminomethyl)-4,5-dihydroisoxazol-3-yl]-7-oxo-1,6-diazabicyclo[3.2.1]octan-6-yl]hydrogen sulfate or a pharmaceutically acceptable salt thereof.

15. The compound of claim 1, wherein the compound is [(2S)-2-[(5R)-5-(aminomethyl)-4,5-dihydroisoxazol-3-yl]-7-oxo-1,6-diazabicyclo[3.2.1]octan-6-yl]hydrogen sulfate or a pharmaceutically acceptable salt thereof.

16. The compound of claim 1, wherein the compound is [(2S)-2-[(5S)-5-(aminomethyl)-4,5-dihydroisoxazol-3-yl]-7-oxo-1,6-diazabicyclo[3.2.1]octan-6-yl]hydrogen sulfate or a pharmaceutically acceptable salt thereof.

17. The compound of claim 1, wherein the compound is [(2S, 5R)-2-(1-oxa-2,7-diazaspiro[4.4]non-2-en-3-yl)-7-oxo-1,6-diazabicyclo[3.2.1]octan-6-yl]hydrogen sulfate or a pharmaceutically acceptable salt thereof.

18. The compound of claim 1, wherein the compound is [(2S,5R)-2-[(5R)-1-oxa-2,7-diazaspiro[4.4]non-2-en-3-yl]-7-oxo-1,6-diazabicyclo[3.2.1]octan-6-yl]hydrogen sulfate or a pharmaceutically acceptable salt thereof.

19. The compound of claim 1, wherein the compound is [(2S,5R)-2-[(5S)-1-oxa-2,7-diazaspiro[4.4]non-2-en-3-yl]-7-oxo-1,6-diazabicyclo[3.2.1]octan-6-yl]hydrogen sulfate or a pharmaceutically acceptable salt thereof.

20. The compound of claim 1, wherein the compound is [(2S, 5R)-2-(5-oxa-2,6-diazaspiro[3.4]oct-6-en-7-yl)-7-oxo-1,6-diazabicyclo[3.2.1]octan-6-yl]hydrogen sulfate or a pharmaceutically acceptable salt thereof.

* * * * *